US010392602B2

(12) United States Patent
Hirayama et al.

(10) Patent No.: US 10,392,602 B2
(45) Date of Patent: Aug. 27, 2019

(54) METHOD OF DERIVING LACRIMAL GLAND EPITHELIAL CELLS FROM ES CELLS AND OTHER STEM CELLS

(71) Applicant: KEIO UNIVERSITY, Tokyo (JP)

(72) Inventors: Masatoshi Hirayama, Tokyo (JP); Minoru Ko, Tokyo (JP)

(73) Assignee: KEIO UNIVERSITY, Tokyo (JP)

( * ) Notice: Subject to any disclaimer, the term of this patent is extended or adjusted under 35 U.S.C. 154(b) by 47 days.

(21) Appl. No.: 15/557,476

(22) PCT Filed: Mar. 25, 2016

(86) PCT No.: PCT/JP2016/059585

§ 371 (c)(1),
(2) Date: Dec. 7, 2017

(87) PCT Pub. No.: WO2016/153027

PCT Pub. Date: Sep. 29, 2016

(65) Prior Publication Data

US 2018/0230425 A1 Aug. 16, 2018

(30) Foreign Application Priority Data

Mar. 25, 2015 (JP) ................................ 2015-062726

(51) Int. Cl.

| | |
|---|---|
| ***A61K 48/00*** | (2006.01) |
| ***C07K 14/00*** | (2006.01) |
| ***C07H 21/04*** | (2006.01) |
| ***C12N 5/00*** | (2006.01) |
| ***C12N 15/63*** | (2006.01) |
| ***C12N 5/079*** | (2010.01) |
| ***C12N 5/10*** | (2006.01) |
| ***C12N 5/074*** | (2010.01) |
| ***C12N 5/16*** | (2006.01) |
| ***C12N 15/85*** | (2006.01) |
| ***C07K 14/47*** | (2006.01) |

(52) U.S. Cl.

CPC ........ *C12N 5/0621* (2013.01); *C07K 14/4702* (2013.01); *C07K 14/4703* (2013.01); *C12N 5/0607* (2013.01); *C12N 5/10* (2013.01); *C12N 5/16* (2013.01); *C12N 15/85* (2013.01); *C07H 21/04* (2013.01); *C12N 15/63* (2013.01); *C12N 2501/01* (2013.01); *C12N 2501/11* (2013.01); *C12N 2501/117* (2013.01); *C12N 2506/02* (2013.01); *C12N 2506/45* (2013.01); *C12N 2510/00* (2013.01)

(58) Field of Classification Search

CPC ....................... C12N 2506/02; C12N 2506/45; C12N 15/63; C12N 2510/00; C07H 21/04; C07K 14/4702

USPC ............... 435/377, 455; 424/93.21; 530/350; 536/23.5

See application file for complete search history.

(56) References Cited

PUBLICATIONS

Romito et al., 2016, Hindawi Publishing Corporation, Stem Cell International, vol. 2016, Article ID 9451492, pp. 1-20.*
Narsinh et al., 2011, Molecular therapy, vol. 9, No. 4, pp. 635-638.*
Bellin et al., 2012, Nature reviews/Molecular Cell Biology, vol. 13, pp. 713-726.*
Burridge et al., 2011, PLoS One, vol. 6, No. 4, e18293, pp. 1-16.*
International Search Report issued in corresponding International Patent Application No. PCT/JP2016/059585 dated May 31, 2016 (2 pages).
International Preliminary Report on Patentability issued in corresponding International Patent Application No. PCT/JP2016/059585 dated Sep. 26, 2017 (5 pages).
Carbe et al., "The functional role of the Meis/Prep-binding elements in Pax6 locus during pancreas and eye development," Developmental Biology, vol. 363, 2012, pp. 320-329.
Hirayama et al., "Direct induction of human lacrimal gland epithelial cell phenotype by introduction of transcription factor," The Japan Ophthalmological Society Journal, vol. 119 Supplemental, 2015, p. 119 with English translation (3 pages).
Katoh et al., "Human FOX gene family (Review)," International Journal of Oncology, vol. 25, No. 5, 2004, pp. 1495-1500 (8 pages).
Laclef et al., "Thymus, kidney and craniofacial abnormalities in Six1 deficient mice," Mechanisms of Development, vol. 120, 2003, pp. 669-679.
Mattiske et al., "The Role of the Forkhead Transcription Factor, Foxc1, in the Development of the Mouse Lacrimal Gland," Developmental Dynamics, vol. 235, 2006, pp. 1074-1080.

* cited by examiner

*Primary Examiner* — Shin Lin Chen
(74) *Attorney, Agent, or Firm* — Kilyk & Bowersox, P.L.L.C.

(57) ABSTRACT

Provided is a method of producing a lacrimal gland epithelial cell from a pluripotent stem cell, a lacrimal gland epithelial cell produced by the method, and a reagent kit for inducing differentiation from a pluripotent stem cell into a lacrimal gland epithelial cell. A method of producing a lacrimal gland epithelial cell includes the following step A: Step A: a step including increasing expression of Pax6 gene in a pluripotent stem cell or transfecting PAX6 protein thereinto, and increasing expression of Foxc1 gene or Foxp1 gene in the pluripotent stem cell or transfecting FOXC1 protein or FOXP1 protein thereinto.

12 Claims, 9 Drawing Sheets

Specification includes a Sequence Listing.

LTF; LACTOFERRIN KRT; CYTOKERATIN AQP5; AQUAPORIN 5

SEQUENCE LISTING

```
<160> NUMBER OF SEQ ID NOS: 16

<210> SEQ ID NO 1
<211> LENGTH: 1269
<212> TYPE: DNA
<213> ORGANISM: Homo sapiens
<220> FEATURE:
<221> NAME/KEY: misc_feature

<400> SEQUENCE: 1

atgcagaaca gtcacagcgg agtgaatcag ctcggtggtg tctttgtcaa cgggcggcca     60

ctgccggact ccacccggca gaagattgta gagctagctc acagcggggc ccggccgtgc    120

gacatttccc gaattctgca ggtgtccaac ggatgtgtga gtaaaattct gggcaggtat    180

tacgagactg gctccatcag acccagggca atcggtggta gtaaaccgag agtagcgact    240

ccagaagttg taagcaaaat agcccagtat aagcgggagt gcccgtccat ctttgcttgg    300

gaaatccgag acagattact gtccgagggg gtctgtacca acgataacat accaagcgtg    360

tcatcaataa acagagttct tcgcaacctg gctagcgaaa agcaacagat gggcgcagac    420

ggcatgtatg ataaactaag gatgttgaac gggcagaccg gaagctgggg cacccgccct    480

ggttggtatc cggggacttc ggtgccaggg caacctacgc aagatggctg ccagcaacag    540

gaaggagggg gagagaatac caactccatc agttccaacg gagaagattc agatgaggct    600

caaatgcgac ttcagctgaa gcggaagctg caaagaaata gaacatcctt tacccaagag    660

caaattgagg ccctggagaa agagtttgag agaacccatt atccagatgt gtttgcccga    720

gaaagactag cagccaaaat agatctacct gaagcaagaa tacaggtatg gttttctaat    780

cgaagggcca aatggagaag agaagaaaaa ctgaggaatc agagaagaca ggccagcaac    840

acacctagtc atattcctat cagcagtagt ttcagcacca gtgtctacca accaattcca    900

caacccacca caccggtttc ctccttcaca tctggctcca tgttgggccg aacagacaca    960

gccctcacaa acacctacag cgctctgccg cctatgccca gcttcaccat ggcaaataac   1020

ctgcctatgc aacccccagt ccccagccag acctcctcat actcctgcat gctgcccacc   1080

agcccttcgg tgaatgggcg gagttatgat acctacaccc ccccacatat gcagacacac   1140

atgaacagtc agccaatggg cacctcgggc accacttcaa caggactcat ttcccctggt   1200

gtgtcagttc cagttcaagt tcccggaagt gaacctgata tgtctcaata ctggccaaga   1260

ttacagtag                                                          1269
```

<210> SEQ ID NO 2
<211> LENGTH: 422
<212> TYPE: PRT
<213> ORGANISM: Homo sapiens

<400> SEQUENCE: 2

```
Met Gln Asn Ser His Ser Gly Val Asn Gln Leu Gly Gly Val Phe Val
1               5                   10                  15

Asn Gly Arg Pro Leu Pro Asp Ser Thr Arg Gln Lys Ile Val Glu Leu
            20                  25                  30

Ala His Ser Gly Ala Arg Pro Cys Asp Ile Ser Arg Ile Leu Gln Val
        35                  40                  45

Ser Asn Gly Cys Val Ser Lys Ile Leu Gly Arg Tyr Tyr Glu Thr Gly
    50                  55                  60

Ser Ile Arg Pro Arg Ala Ile Gly Gly Ser Lys Pro Arg Val Ala Thr
65                  70                  75                  80

Pro Glu Val Val Ser Lys Ile Ala Gln Tyr Lys Arg Glu Cys Pro Ser
                85                  90                  95

Ile Phe Ala Trp Glu Ile Arg Asp Arg Leu Leu Ser Glu Gly Val Cys
            100                 105                 110

Thr Asn Asp Asn Ile Pro Ser Val Ser Ser Ile Asn Arg Val Leu Arg
        115                 120                 125

Asn Leu Ala Ser Glu Lys Gln Gln Met Gly Ala Asp Gly Met Tyr Asp
    130                 135                 140

Lys Leu Arg Met Leu Asn Gly Gln Thr Gly Ser Trp Gly Thr Arg Pro
145                 150                 155                 160

Gly Trp Tyr Pro Gly Thr Ser Val Pro Gly Gln Pro Thr Gln Asp Gly
                165                 170                 175

Cys Gln Gln Gln Glu Gly Gly Gly Glu Asn Thr Asn Ser Ile Ser Ser
            180                 185                 190

Asn Gly Glu Asp Ser Asp Glu Ala Gln Met Arg Leu Gln Leu Lys Arg
        195                 200                 205

Lys Leu Gln Arg Asn Arg Thr Ser Phe Thr Gln Glu Gln Ile Glu Ala
    210                 215                 220

Leu Glu Lys Glu Phe Glu Arg Thr His Tyr Pro Asp Val Phe Ala Arg
225                 230                 235                 240

Glu Arg Leu Ala Ala Lys Ile Asp Leu Pro Glu Ala Arg Ile Gln Val
                245                 250                 255

Trp Phe Ser Asn Arg Arg Ala Lys Trp Arg Arg Glu Glu Lys Leu Arg
            260                 265                 270

Asn Gln Arg Arg Gln Ala Ser Asn Thr Pro Ser His Ile Pro Ile Ser
        275                 280                 285

Ser Ser Phe Ser Thr Ser Val Tyr Gln Pro Ile Pro Gln Pro Thr Thr
    290                 295                 300

Pro Val Ser Ser Phe Thr Ser Gly Ser Met Leu Gly Arg Thr Asp Thr
305                 310                 315                 320

Ala Leu Thr Asn Thr Tyr Ser Ala Leu Pro Pro Met Pro Ser Phe Thr
                325                 330                 335

Met Ala Asn Asn Leu Pro Met Gln Pro Pro Val Pro Ser Gln Thr Ser
            340                 345                 350

Ser Tyr Ser Cys Met Leu Pro Thr Ser Pro Ser Val Asn Gly Arg Ser
        355                 360                 365

Tyr Asp Thr Tyr Thr Pro Pro His Met Gln Thr His Met Asn Ser Gln
    370                 375                 380
```

```
Pro Met Gly Thr Ser Gly Thr Thr Ser Thr Gly Leu Ile Ser Pro Gly
385                 390                 395                 400

Val Ser Val Pro Val Gln Val Pro Gly Ser Glu Pro Asp Met Ser Gln
                405                 410                 415

Tyr Trp Pro Arg Leu Gln
            420


<210> SEQ ID NO 3
<211> LENGTH: 1662
<212> TYPE: DNA
<213> ORGANISM: Homo sapiens

<400> SEQUENCE: 3

atgcaggcgc gctactccgt gtccagcccc aactccctgg gagtggtgcc ctacctcggc      60

ggcgagcaga gctactaccg cgcggcggcc gcggcggccg ggggcggcta caccgccatg     120

ccggccccca tgagcgtgta ctcgcaccct gcgcacgccg agcagtaccc gggcggcatg     180

gcccgcgcct acgggcccta cacgccgcag ccgcagccca aggacatggt gaagccgccc     240

tatagctaca tcgcgctcat caccatggcc atccagaacg ccccggacaa gaagatcacc     300

ctgaacggca tctaccagtt catcatggac cgcttcccct tctaccggga caacaagcag     360

ggctggcaga acagcatccg ccacaacctc tcgctcaacg agtgcttcgt caaggtgccg     420

cgcgacgaca agaagccggg caagggcagc tactggacgc tggacccgga ctcctacaac     480

atgttcgaga acggcagctt cctgcggcgg cggcggcgct tcaagaagaa ggacgcggtg     540

aaggacaagg aggagaagga caggctgcac ctcaaggagc cgcccccgcc cggccgccag     600

cccccgcccg cgccgccgga gcaggccgac ggcaacgcgc ccggtccgca gccgccgccc     660

gtgcgcatcc aggacatcaa gaccgagaac ggtacgtgcc cctcgccgcc ccagcccctg     720

tccccggccg ccgccctggg cagcggcagc gccgccgcgg tgcccaagat cgagagcccc     780

gacagcagca gcagcagcct gtccagcggg agcagccccc cgggcagcct gccgtcggcg     840

cggccgctca gcctggacgg tgcggattcc gcgccgccgc cgcccgcgcc ctccgccccg     900

ccgccgcacc atagccaggg cttcagcgtg gacaacatca tgacgtcgct gcgggggtcg     960

ccgcagagcg cggccgcgga gctcagctcc ggccttctgg cctcggcggc cgcgtcctcg    1020

cgcgcgggga tcgcaccccc gctggcgctc ggcgcctact cgcccggcca gagctccctc    1080

tacagctccc cctgcagcca gacctccagc gcgggcagct cgggcggcgg cggcggcggc    1140

gcgggggccg cgggggcgc gggcggcgcc gggacctacc actgcaacct gcaagccatg    1200

agcctgtacg cggccggcga gcgcgggggc cacttgcagg gcgcgcccgg gggcgcgggc    1260

ggctcggccg tggacgaccc cctgcccgac tactctctgc ctccggtcac cagcagcagc    1320

tcgtcgtccc tgagtcacgg cggcggcggc ggcggcggcg ggggaggcca ggaggccggc    1380

caccaccctg cggcccacca aggccgcctc acctcgtggt acctgaacca ggcgggcgga    1440

gacctgggcc acttggcgag cgcggcggcg gcggcggcgg ccgcaggcta cccgggccag    1500

cagcagaact tccactcggt gcgggagatg ttcgagtcac agaggatcgg cttgaacaac    1560

tctccagtga acgggaatag tagctgtcaa atggccttcc cttccagcca gtctctgtac    1620

cgcacgtccg gagctttcgt ctacgactgt agcaagtttt ag                       1662


<210> SEQ ID NO 4
<211> LENGTH: 553
<212> TYPE: PRT
<213> ORGANISM: Homo sapiens
```

<400> SEQUENCE: 4

```
Met Gln Ala Arg Tyr Ser Val Ser Ser Pro Asn Ser Leu Gly Val Val
1               5                   10                  15

Pro Tyr Leu Gly Gly Glu Gln Ser Tyr Tyr Arg Ala Ala Ala Ala Ala
            20                  25                  30

Ala Gly Gly Gly Tyr Thr Ala Met Pro Ala Pro Met Ser Val Tyr Ser
        35                  40                  45

His Pro Ala His Ala Glu Gln Tyr Pro Gly Gly Met Ala Arg Ala Tyr
    50                  55                  60

Gly Pro Tyr Thr Pro Gln Pro Gln Pro Lys Asp Met Val Lys Pro Pro
65                  70                  75                  80

Tyr Ser Tyr Ile Ala Leu Ile Thr Met Ala Ile Gln Asn Ala Pro Asp
                85                  90                  95

Lys Lys Ile Thr Leu Asn Gly Ile Tyr Gln Phe Ile Met Asp Arg Phe
            100                 105                 110

Pro Phe Tyr Arg Asp Asn Lys Gln Gly Trp Gln Asn Ser Ile Arg His
        115                 120                 125

Asn Leu Ser Leu Asn Glu Cys Phe Val Lys Val Pro Arg Asp Asp Lys
    130                 135                 140

Lys Pro Gly Lys Gly Ser Tyr Trp Thr Leu Asp Pro Asp Ser Tyr Asn
145                 150                 155                 160

Met Phe Glu Asn Gly Ser Phe Leu Arg Arg Arg Arg Arg Phe Lys Lys
                165                 170                 175

Lys Asp Ala Val Lys Asp Lys Glu Glu Lys Asp Arg Leu His Leu Lys
            180                 185                 190

Glu Pro Pro Pro Pro Gly Arg Gln Pro Pro Pro Ala Pro Pro Glu Gln
        195                 200                 205

Ala Asp Gly Asn Ala Pro Gly Pro Gln Pro Pro Pro Val Arg Ile Gln
    210                 215                 220

Asp Ile Lys Thr Glu Asn Gly Thr Cys Pro Ser Pro Pro Gln Pro Leu
225                 230                 235                 240

Ser Pro Ala Ala Ala Leu Gly Ser Gly Ser Ala Ala Ala Val Pro Lys
                245                 250                 255

Ile Glu Ser Pro Asp Ser Ser Ser Ser Ser Leu Ser Ser Gly Ser Ser
            260                 265                 270

Pro Pro Gly Ser Leu Pro Ser Ala Arg Pro Leu Ser Leu Asp Gly Ala
        275                 280                 285

Asp Ser Ala Pro Pro Pro Pro Ala Pro Ser Ala Pro Pro Pro His His
    290                 295                 300

Ser Gln Gly Phe Ser Val Asp Asn Ile Met Thr Ser Leu Arg Gly Ser
305                 310                 315                 320

Pro Gln Ser Ala Ala Ala Glu Leu Ser Ser Gly Leu Leu Ala Ser Ala
                325                 330                 335

Ala Ala Ser Ser Arg Ala Gly Ile Ala Pro Pro Leu Ala Leu Gly Ala
            340                 345                 350

Tyr Ser Pro Gly Gln Ser Ser Leu Tyr Ser Ser Pro Cys Ser Gln Thr
        355                 360                 365

Ser Ser Ala Gly Ser Ser Gly Gly Gly Gly Gly Gly Ala Gly Ala Ala
    370                 375                 380

Gly Gly Ala Gly Gly Ala Gly Thr Tyr His Cys Asn Leu Gln Ala Met
385                 390                 395                 400

Ser Leu Tyr Ala Ala Gly Glu Arg Gly Gly His Leu Gln Gly Ala Pro
```

```
                405                 410                 415

Gly Gly Ala Gly Gly Ser Ala Val Asp Asp Pro Leu Pro Asp Tyr Ser
            420                 425                 430

Leu Pro Pro Val Thr Ser Ser Ser Ser Ser Ser Leu Ser His Gly Gly
        435                 440                 445

Gly Gly Gly Gly Gly Gly Gly Gly Gln Glu Ala Gly His His Pro Ala
    450                 455                 460

Ala His Gln Gly Arg Leu Thr Ser Trp Tyr Leu Asn Gln Ala Gly Gly
465                 470                 475                 480

Asp Leu Gly His Leu Ala Ser Ala Ala Ala Ala Ala Ala Ala Ala Gly
                485                 490                 495

Tyr Pro Gly Gln Gln Gln Asn Phe His Ser Val Arg Glu Met Phe Glu
            500                 505                 510

Ser Gln Arg Ile Gly Leu Asn Asn Ser Pro Val Asn Gly Asn Ser Ser
        515                 520                 525

Cys Gln Met Ala Phe Pro Ser Ser Gln Ser Leu Tyr Arg Thr Ser Gly
    530                 535                 540

Ala Phe Val Tyr Asp Cys Ser Lys Phe
545                 550
```

<210> SEQ ID NO 5
<211> LENGTH: 2034
<212> TYPE: DNA
<213> ORGANISM: Homo sapiens

<400> SEQUENCE: 5

```
atgatgcaag aatctgggac tgagacaaaa agtaacggtt cagccatcca gaatgggtcg     60

ggcggcagca accacttact agagtgcggc ggtcttcggg aggggcggtc caacggagag    120

acgccggccg tggacatcgg ggcagctgac ctcgcccacg cccagcagca gcagcaacag    180

gcacttcagg tggcaagaca gctccttctt cagcagcaac agcagcagca agttagtgga    240

ttaaaatctc ccaaggggaa tgacaaacaa ccagctcttc aggttcccgt gtcagtggct    300

atgatgacac ctcaagttat cactccccag caaatgcagc agatcctcca gcaacaagtg    360

ctgagccctc agcagctcca ggttctcctc cagcagcagc aggccctcat gcttcaacag    420

cagcagcttc aagagtttta taaaaaacaa caggaacagt tgcagcttca acttttacaa    480

caacaacatg ctggaaaaca gcctaaagag caacagcagg tggctaccca gcagttggct    540

tttcagcagc agcttttaca gatgcagcag ttacagcagc agcacctcct gtctttgcag    600

cgccaaggcc ttctgacaat tcagcccggg cagcctgccc ttccccttca acctcttgct    660

caaggcatga ttccaacaga actgcagcag ctctggaaag aagtgacaag tgctcatact    720

gcagaagaaa ccacaggcaa caatcacagc agtttggatc tgaccacgac atgtgtctcc    780

tcctctgcac cttccaagac ctccttaata atgaacccac atgcctctac caatggacag    840

ctctcagtcc acactcccaa aagggaaagt ttgtcccatg aggagcaccc ccatagccat    900

cctctctatg gacatggtgt atgcaagtgg ccaggctgtg aagcagtgtg cgaagatttc    960

caatcatttc taaaacatct caacagtgag catgcgctgg acgatagaag tacagcccaa   1020

tgtagagtac aaatgcaggt tgtacagcag ttagagctac agcttgcaaa agacaaagaa   1080

cgcctgcaag ccatgatgac ccacctgcat gtgaagtcta cagaacccaa agccgcccct   1140

cagcccttga atctggtatc aagtgtcact ctctccaagt ccgcatcgga ggcttctcca   1200

cagagcatac ctcatactcc aacgacccca accgcccccc tgactcccgt cacccaaggc   1260
```

-continued

```
ccctctgtca tcacaaccac cagcatgcac acggtgggac ccatccgcag gcggtactca   1320

gacaaataca acgtgcccat ttcgtcagca gatattgcgc agaaccaaga attttataag   1380

aacgcagaag ttagaccacc atttacatat gcatctttaa ttaggcaggc cattctcgaa   1440

tctccagaaa agcagctaac gctaaatgag atctataact ggttcacacg aatgtttgct   1500

tacttccgac gcaacgcggc cacgtggaag aatgcagtgc gtcataatct tagtcttcac   1560

aagtgttttg tgcgagtaga aaacgttaaa ggggcagtat ggacagtgga tgaagtagaa   1620

ttccaaaaac gaaggccaca aaagatcagt ggtaaccctt cccttattaa aaacatgcag   1680

agcagccacg cctactgcac acctctcaat gcagctttac aggcttcaat ggctgagaat   1740

agtatacctc tatacactac cgcttccatg ggaaatccca ctctgggcaa cttagccagc   1800

gcaatacggg aagagctgaa cggggcaatg gagcatacca acagcaacga gagtgacagc   1860

agtccaggca gatctcctat gcaagccgtg catcctgtac acgtcaaaga agagcccctc   1920

gatccagagg aagctgaagg gcccctgtcc ttagtgacaa cagccaacca cagtccagat   1980

tttgaccatg acagagatta cgaagatgaa ccagtaaacg aggacatgga gtga         2034
```

<210> SEQ ID NO 6
<211> LENGTH: 677
<212> TYPE: PRT
<213> ORGANISM: Homo sapiens

<400> SEQUENCE: 6

```
Met Met Gln Glu Ser Gly Thr Glu Thr Lys Ser Asn Gly Ser Ala Ile
1               5                   10                  15

Gln Asn Gly Ser Gly Gly Ser Asn His Leu Leu Glu Cys Gly Gly Leu
            20                  25                  30

Arg Glu Gly Arg Ser Asn Gly Glu Thr Pro Ala Val Asp Ile Gly Ala
        35                  40                  45

Ala Asp Leu Ala His Ala Gln Gln Gln Gln Gln Gln Ala Leu Gln Val
    50                  55                  60

Ala Arg Gln Leu Leu Leu Gln Gln Gln Gln Gln Gln Gln Val Ser Gly
65                  70                  75                  80

Leu Lys Ser Pro Lys Gly Asn Asp Lys Gln Pro Ala Leu Gln Val Pro
                85                  90                  95

Val Ser Val Ala Met Met Thr Pro Gln Val Ile Thr Pro Gln Gln Met
            100                 105                 110

Gln Gln Ile Leu Gln Gln Gln Val Leu Ser Pro Gln Gln Leu Gln Val
        115                 120                 125

Leu Leu Gln Gln Gln Gln Ala Leu Met Leu Gln Gln Gln Gln Leu Gln
    130                 135                 140

Glu Phe Tyr Lys Lys Gln Gln Glu Gln Leu Gln Leu Gln Leu Leu Gln
145                 150                 155                 160

Gln Gln His Ala Gly Lys Gln Pro Lys Glu Gln Gln Gln Val Ala Thr
                165                 170                 175

Gln Gln Leu Ala Phe Gln Gln Gln Leu Leu Gln Met Gln Gln Leu Gln
            180                 185                 190

Gln Gln His Leu Leu Ser Leu Gln Arg Gln Gly Leu Leu Thr Ile Gln
        195                 200                 205

Pro Gly Gln Pro Ala Leu Pro Leu Gln Pro Leu Ala Gln Gly Met Ile
    210                 215                 220

Pro Thr Glu Leu Gln Gln Leu Trp Lys Glu Val Thr Ser Ala His Thr
225                 230                 235                 240
```

```
Ala Glu Glu Thr Thr Gly Asn Asn His Ser Ser Leu Asp Leu Thr Thr
                245                 250                 255

Thr Cys Val Ser Ser Ser Ala Pro Ser Lys Thr Ser Leu Ile Met Asn
            260                 265                 270

Pro His Ala Ser Thr Asn Gly Gln Leu Ser Val His Thr Pro Lys Arg
        275                 280                 285

Glu Ser Leu Ser His Glu Glu His Pro His Ser His Pro Leu Tyr Gly
    290                 295                 300

His Gly Val Cys Lys Trp Pro Gly Cys Glu Ala Val Cys Glu Asp Phe
305                 310                 315                 320

Gln Ser Phe Leu Lys His Leu Asn Ser Glu His Ala Leu Asp Asp Arg
                325                 330                 335

Ser Thr Ala Gln Cys Arg Val Gln Met Gln Val Val Gln Gln Leu Glu
            340                 345                 350

Leu Gln Leu Ala Lys Asp Lys Glu Arg Leu Gln Ala Met Met Thr His
        355                 360                 365

Leu His Val Lys Ser Thr Glu Pro Lys Ala Ala Pro Gln Pro Leu Asn
    370                 375                 380

Leu Val Ser Ser Val Thr Leu Ser Lys Ser Ala Ser Glu Ala Ser Pro
385                 390                 395                 400

Gln Ser Ile Pro His Thr Pro Thr Thr Pro Thr Ala Pro Leu Thr Pro
                405                 410                 415

Val Thr Gln Gly Pro Ser Val Ile Thr Thr Thr Ser Met His Thr Val
            420                 425                 430

Gly Pro Ile Arg Arg Arg Tyr Ser Asp Lys Tyr Asn Val Pro Ile Ser
        435                 440                 445

Ser Ala Asp Ile Ala Gln Asn Gln Glu Phe Tyr Lys Asn Ala Glu Val
    450                 455                 460

Arg Pro Pro Phe Thr Tyr Ala Ser Leu Ile Arg Gln Ala Ile Leu Glu
465                 470                 475                 480

Ser Pro Glu Lys Gln Leu Thr Leu Asn Glu Ile Tyr Asn Trp Phe Thr
                485                 490                 495

Arg Met Phe Ala Tyr Phe Arg Arg Asn Ala Ala Thr Trp Lys Asn Ala
            500                 505                 510

Val Arg His Asn Leu Ser Leu His Lys Cys Phe Val Arg Val Glu Asn
        515                 520                 525

Val Lys Gly Ala Val Trp Thr Val Asp Glu Val Glu Phe Gln Lys Arg
    530                 535                 540

Arg Pro Gln Lys Ile Ser Gly Asn Pro Ser Leu Ile Lys Asn Met Gln
545                 550                 555                 560

Ser Ser His Ala Tyr Cys Thr Pro Leu Asn Ala Ala Leu Gln Ala Ser
                565                 570                 575

Met Ala Glu Asn Ser Ile Pro Leu Tyr Thr Thr Ala Ser Met Gly Asn
            580                 585                 590

Pro Thr Leu Gly Asn Leu Ala Ser Ala Ile Arg Glu Glu Leu Asn Gly
        595                 600                 605

Ala Met Glu His Thr Asn Ser Asn Glu Ser Asp Ser Ser Pro Gly Arg
    610                 615                 620

Ser Pro Met Gln Ala Val His Pro Val His Val Lys Glu Glu Pro Leu
625                 630                 635                 640

Asp Pro Glu Glu Ala Glu Gly Pro Leu Ser Leu Val Thr Thr Ala Asn
                645                 650                 655

His Ser Pro Asp Phe Asp His Asp Arg Asp Tyr Glu Asp Glu Pro Val
```

```
            660                 665                 670

Asn Glu Asp Met Glu
        675


<210> SEQ ID NO 7
<211> LENGTH: 855
<212> TYPE: DNA
<213> ORGANISM: Homo sapiens

<400> SEQUENCE: 7

atgtcgatgc tgccgtcgtt tggctttacg caggagcaag tggcgtgcgt gtgcgaggtt      60

ctgcagcaag gcggaaacct ggagcgcctg ggcaggttcc tgtggtcact gcccgcctgc     120

gaccacctgc acaagaacga gagcgtactc aaggccaagg cggtggtcgc cttccaccgc     180

ggcaacttcc gtgagctcta caagatcctg gagagccacc agttctcgcc tcacaaccac     240

cccaaactgc agcaactgtg gctgaaggcg cattacgtgg aggccgagaa gctgtgcggc     300

cgacccctgg gcgccgtggg caaatatcgg gtgcgccgaa aatttccact gccgcgcacc     360

atctgggacg gcgaggagac cagctactgc ttcaaggaga agtcgagggg tgtcctgcgg     420

gagtggtacg cgcacaatcc ctacccatcg ccgcgtgaga agcgggagct ggccgaggcc     480

accggcctca ccaccaccca ggtcagcaac tggtttaaga accggaggca aagagaccgg     540

gccgcggagg ccaaggaaag ggagaacacc gaaaacaata actcctcctc caacaagcag     600

aaccaactct ctcctctgga aggggggcaag ccgctcatgt ccagctcaga agaggaattc     660

tcacctcccc aaagtccaga ccagaactcg gtccttctgc tgcagggcaa tatgggccac     720

gccaggagct caaactattc tctcccgggc ttaacagcct cgcagcccag tcacggcctg     780

cagacccacc agcatcagct ccaagactct ctgctcggcc ccctcacctc cagtctggtg     840

gacttggggt cctaa                                                      855


<210> SEQ ID NO 8
<211> LENGTH: 284
<212> TYPE: PRT
<213> ORGANISM: Homo sapiens

<400> SEQUENCE: 8

Met Ser Met Leu Pro Ser Phe Gly Phe Thr Gln Glu Gln Val Ala Cys
1               5                   10                  15

Val Cys Glu Val Leu Gln Gln Gly Gly Asn Leu Glu Arg Leu Gly Arg
            20                  25                  30

Phe Leu Trp Ser Leu Pro Ala Cys Asp His Leu His Lys Asn Glu Ser
        35                  40                  45

Val Leu Lys Ala Lys Ala Val Val Ala Phe His Arg Gly Asn Phe Arg
    50                  55                  60

Glu Leu Tyr Lys Ile Leu Glu Ser His Gln Phe Ser Pro His Asn His
65                  70                  75                  80

Pro Lys Leu Gln Gln Leu Trp Leu Lys Ala His Tyr Val Glu Ala Glu
                85                  90                  95

Lys Leu Cys Gly Arg Pro Leu Gly Ala Val Gly Lys Tyr Arg Val Arg
            100                 105                 110

Arg Lys Phe Pro Leu Pro Arg Thr Ile Trp Asp Gly Glu Glu Thr Ser
        115                 120                 125

Tyr Cys Phe Lys Glu Lys Ser Arg Gly Val Leu Arg Glu Trp Tyr Ala
    130                 135                 140

His Asn Pro Tyr Pro Ser Pro Arg Glu Lys Arg Glu Leu Ala Glu Ala
```

-continued

```
145                 150                 155                 160

Thr Gly Leu Thr Thr Thr Gln Val Ser Asn Trp Phe Lys Asn Arg Arg
                165                 170                 175

Gln Arg Asp Arg Ala Ala Glu Ala Lys Glu Arg Glu Asn Thr Glu Asn
            180                 185                 190

Asn Asn Ser Ser Ser Asn Lys Gln Asn Gln Leu Ser Pro Leu Glu Gly
        195                 200                 205

Gly Lys Pro Leu Met Ser Ser Ser Glu Glu Glu Phe Ser Pro Pro Gln
    210                 215                 220

Ser Pro Asp Gln Asn Ser Val Leu Leu Leu Gln Gly Asn Met Gly His
225                 230                 235                 240

Ala Arg Ser Ser Asn Tyr Ser Leu Pro Gly Leu Thr Ala Ser Gln Pro
                245                 250                 255

Ser His Gly Leu Gln Thr His Gln His Gln Leu Gln Asp Ser Leu Leu
            260                 265                 270

Gly Pro Leu Thr Ser Ser Leu Val Asp Leu Gly Ser
        275                 280


<210> SEQ ID NO 9
<211> LENGTH: 20
<212> TYPE: DNA
<213> ORGANISM: Artificial
<220> FEATURE:
<223> OTHER INFORMATION: Pax6 Forward primer

<400> SEQUENCE: 9

cagaacagtc acagcggagt                                               20


<210> SEQ ID NO 10
<211> LENGTH: 20
<212> TYPE: DNA
<213> ORGANISM: Artificial
<220> FEATURE:
<223> OTHER INFORMATION: Pax6 Reverse primer

<400> SEQUENCE: 10

ttgctggcct gtcttctctg                                               20


<210> SEQ ID NO 11
<211> LENGTH: 20
<212> TYPE: DNA
<213> ORGANISM: Artificial
<220> FEATURE:
<223> OTHER INFORMATION: Foxc1 Forward primer

<400> SEQUENCE: 11

tatactgcgg gttggaaagg                                               20


<210> SEQ ID NO 12
<211> LENGTH: 21
<212> TYPE: DNA
<213> ORGANISM: Artificial
<220> FEATURE:
<223> OTHER INFORMATION: Foxc1 Reverse primer

<400> SEQUENCE: 12

tgtaatcaaa tcgccatctc c                                             21


<210> SEQ ID NO 13
<211> LENGTH: 20
<212> TYPE: DNA
<213> ORGANISM: Artificial
```

-continued

```
<220> FEATURE:
<223> OTHER INFORMATION: Foxp1 Forward primer

<400> SEQUENCE: 13

ttcaggggta agacgtgacc                                                20


<210> SEQ ID NO 14
<211> LENGTH: 20
<212> TYPE: DNA
<213> ORGANISM: Artificial
<220> FEATURE:
<223> OTHER INFORMATION: Foxp1 Reverse primer

<400> SEQUENCE: 14

taacttgctg ctgctgttgc                                                20


<210> SEQ ID NO 15
<211> LENGTH: 21
<212> TYPE: DNA
<213> ORGANISM: Artificial
<220> FEATURE:
<223> OTHER INFORMATION: Six1 Forward primer

<400> SEQUENCE: 15

caaagtccag accagaactc g                                              21


<210> SEQ ID NO 16
<211> LENGTH: 20
<212> TYPE: DNA
<213> ORGANISM: Artificial
<220> FEATURE:
<223> OTHER INFORMATION: Six1 Reverse primer

<400> SEQUENCE: 16

gggtgctttt gtttgtttgg                                                20
```

METHOD OF DERIVING LACRIMAL GLAND EPITHELIAL CELLS FROM ES CELLS AND OTHER STEM CELLS

TECHNICAL FIELD

The present invention relates to a method of producing a lacrimal gland epithelial cell from a pluripotent stem cell, a lacrimal gland epithelial cell produced by the method, and a reagent kit for inducing differentiation from a pluripotent stem cell into a lacrimal gland epithelial cell.

The present application is a National Stage Application of PCT/JP2016/059585, filed Mar. 25, 2016, which claims priority from Japanese Patent Application No. 2015-062726, which is incorporated herein by reference.

BACKGROUND ART

Dry eye, which is also called xerophthalmia or dry eye syndrome, is a disease in which a reduction or impairment in tear secretory function of a lacrimal gland, or the like causes a quantitative and/or qualitative abnormality in tears, resulting in an impairment in an ocular surface, that is, cornea and conjunctiva. As a cause of the reduction or impairment in tear secretory function of the lacrimal gland, there are known, for example, video display terminal work (VDT work), aging, and a disease involving inflammation in the lacrimal gland. As such disease, there are known, for example, an autoimmune disorder, such as Sjögren's syndrome, keratoconjunctivitis sicca, Stevens-Johnson syndrome, and marginal blepharitis. When inflammation occurs in the lacrimal gland, inflammatory cells, such as lymphocytes, infiltrate the lacrimal gland to cause the reduction or impairment in tear secretory function of the lacrimal gland. It is said that there are 8,000,000 or more dry eye patients, including potential patients, in Japan, and the increase in dry eye has even become a social problem.

As a method of ameliorating dry eye, a method involving administering artificial tears is generally used. However, the method is only a symptomatic treatment. In addition, its effect is temporary, and hence the method has been troublesome to patients owing to, for example, a need for as many as from 10 times to 20 times of application a day. In addition, in order to alleviate an inflammatory response in the disease involving inflammation in the lacrimal gland, a drug, such as a steroid or ciclosporin, is used, but cannot improve a secretion amount of tears to a normal condition.

In view of the foregoing, a search for tissue stem cells (adult stem cells) of the lacrimal gland has been advanced in order to achieve a stem cell transplantation therapy capable of restoring an impaired lacrimal gland tissue to realize fundamental recovery of the lacrimal gland function. However, tissue stem cells of the lacrimal gland that have an ability to form a lacrimal gland organ have yet to be isolated.

In addition, the inventors of the present invention previously produced a regenerated lacrimal gland germ to be developed into a lacrimal gland from lacrimal gland epithelial cells and lacrimal gland mesenchymal cells derived from a lacrimal gland germ of a mouse embryo by an organ-germ method (Non Patent Literature 1: Nat. Methods 4, 227-230 (2007)), and implanted such regenerated lacrimal gland germ into a site of lacrimal gland loss in a model mouse having its lacrimal gland function impaired, to thereby reveal that a functional lacrimal gland was able to be regenerated (Non Patent Literature 2: Nature Communications 4, 2497 (2013), doi:10.1038/ncomms3497). This method enables lacrimal gland organ regeneration, but in consideration of future clinical application in humans, has had a problem of requiring a technology for deriving a lacrimal gland from a clinically applicable cell source, such as embryonic stem cells (ES cells) or induced pluripotent stem cells (iPS cells). Under such technical circumstances, there has yet to be made a report of successful derivation from ES cells or iPS cells into lacrimal gland epithelial cells or lacrimal gland mesenchymal cells.

CITATION LIST

Non Patent Literature

[NPL 1] Nat. Methods 4, 227-230 (2007)

[NPL 2] Nature Communications 4, 2497 (2013), doi: 10.1038/ncomms3497

SUMMARY OF INVENTION

Technical Problem

It is an object of the present invention to provide a method of producing a lacrimal gland epithelial cell from a pluripotent stem cell, a lacrimal gland epithelial cell produced by the method, and a reagent kit for inducing differentiation from a pluripotent stem cell into a lacrimal gland epithelial cell.

Solution to Problem

The inventors of the present invention analyzed the expression of various mRNAs in eight kinds of cells, including lacrimal gland epithelial cells, with a microarray to identify genes highly expressed specifically in the lacrimal gland epithelial cells. The inventors of the present invention focused on two kinds of transcription factors (Six2 and Foxc1) among those identified genes. The inventors of the present invention focused also on Six1, Six4, and Foxc2 as transcription factor genes exhibiting similar expression tendencies to that of the Six2 gene in the eight kinds of cells. The inventors of the present invention focused also on Foxp1 gene, Runx1 gene, and ILF2 gene as transcription factor genes exhibiting similar expression tendencies to those of Pax6 gene and the Foxc1 gene.

The inventors of the present invention took those nine kinds of genes on which the inventors focused as candidate genes and artificially synthesized the respective mRNAs of those candidate genes. The inventors transfected those mRNAs in various combinations into human ES cells, cultured the human ES cells, and confirmed the expression of a group of marker genes of lacrimal gland epithelial cells. As a result, the inventors found that, when the mRNA of the Pax6 gene and the mRNA of the Foxc1 gene were transfected, and when the mRNA of the Pax6 gene and the mRNA of the Foxp1 gene were transfected, the expression of the group of marker genes of lacrimal gland epithelial cells was confirmed. Then, when the mRNA of the Pax6 gene and the mRNA of the Foxp1 gene were transfected, an increase in expression of the Foxc1 gene was confirmed. Thus, the inventors of the present invention found that increases in expression of the Pax6 gene and the Foxc1 gene in pluripotent stem cells were ultimately essential for inducing differentiation into lacrimal gland epithelial cells. It was extremely surprising even to a person skilled in the art that differentiation from pluripotent stem cells into lacrimal gland epithelial cells was able to be induced by increasing the expression of only two kinds of genes. Further, the inventors of the present invention found that, when the mRNA of the Six1 gene was transfected in addition to the mRNA of the Pax6 gene and the mRNA of the Foxc1 gene, the expression of Barx2 gene, which was one of the lacrimal gland epithelial cell marker genes, was more enhanced to make more distinct a morphological change into lacrimal gland epithelial cells, and thus the direction of differentiation into a lacrimal gland epithelial cell line was able to be made more distinct.

In addition, when the inventors of the present invention co-cultured lacrimal gland epithelial cells produced by transfecting the mRNAs of the above-mentioned specific two kinds or three kinds of genes with lacrimal gland germ cells of a mouse embryo in order to confirm whether the above-mentioned lacrimal gland epithelial cells had an ability to regenerate the three-dimensional structure of a lacrimal gland organ, a three-dimensional structure similar to a mature lacrimal gland was formed. Thus, it was shown that the lacrimal gland epithelial cells produced by the method of the present invention had an ability to regenerate the three-dimensional structure of a lacrimal gland organ.

The inventors of the present invention have completed the present invention on the basis of the above-mentioned findings.

That is, the present invention is as described below.

1. A method of producing a lacrimal gland epithelial cell, including the following step A:

Step A: a step including increasing expression of Pax6 gene in a pluripotent stem cell or transfecting PAX6 protein thereinto, and increasing expression of Foxc1 gene or Foxp1 gene in the pluripotent stem cell or transfecting FOXC1 protein or FOXP1 protein thereinto.

2. A method of producing a lacrimal gland epithelial cell according to the above-mentioned item 1, in which the step of increasing expression of Pax6 gene includes a step of transfecting a polynucleotide encoding PAX6 protein into the pluripotent stem cell, in which the step of increasing expression of Foxc1 gene includes a step of transfecting a polynucleotide encoding FOXC1 protein into the pluripotent stem cell, and in which the step of increasing expression of Foxp1 gene includes a step of transfecting a polynucleotide encoding FOXP1 protein into the pluripotent stem cell.

3. A method of producing a lacrimal gland epithelial cell according to the above-mentioned item 1 or 2, in which the step A further includes increasing expression of Six1 gene in the pluripotent stem cell or transfecting SIX1 protein thereinto.

4. A method of producing a lacrimal gland epithelial cell according to the above-mentioned item 3, in which the increasing expression of Six1 gene includes transfecting a polynucleotide encoding SIX1 protein into the pluripotent stem cell.

5. A method of producing a lacrimal gland epithelial cell according to any one of the above-mentioned items 1 to 4, further including a step of culturing the cell obtained in the step A in a keratinocyte growth medium.

6. A method of producing a lacrimal gland epithelial cell according to the above-mentioned item 5, in which the keratinocyte growth medium contains epidermal growth factor and/or cholera toxin.

7. A method of producing a lacrimal gland epithelial cell according to the above-mentioned item 5 or 6, in which the keratinocyte growth medium has a calcium concentration of 0.15 mM or less.

8. A method of producing a lacrimal gland epithelial cell according to any one of the above-mentioned items 2 to 7, in which the polynucleotide includes mRNA.

9. A lacrimal gland epithelial cell, which is produced by the method of producing a lacrimal gland epithelial cell of any one of the above-mentioned items 1 to 8.

10. A lacrimal gland epithelial cell according to the above-mentioned item 9, in which the lacrimal gland epithelial cell has an ability to regenerate a three-dimensional structure of a lacrimal gland organ.

11. A reagent kit for inducing differentiation from a pluripotent stem cell into a lacrimal gland epithelial cell, including the following (a) and (b):

(a) a polynucleotide encoding PAX6 protein, or PAX6 protein; and (b) a polynucleotide encoding FOXC1 protein, or FOXC1 protein, or a polynucleotide encoding FOXP1 protein, or FOXP1 protein.

12. A reagent kit for inducing differentiation according to the above-mentioned item 11, further including (c) a polynucleotide encoding SIX1 protein, or SIX1 protein.

Advantageous Effects of Invention

According to the hitherto known findings, in order to regenerate a lacrimal gland organ, it has been necessary that its materials, i.e., lacrimal gland epithelial cells and lacrimal gland mesenchymal cells be procured by being harvested from an embryonic mammal (Non Patent Literature 2). According to the present invention, the lacrimal gland epithelial cells can be produced efficiently in a large amount within a short period of time from clinically applicable pluripotent stem cells (e.g., ES cells or iPS cells). In addition, the lacrimal gland epithelial cell produced by the present invention is a lacrimal gland epithelial cell having an ability to regenerate the three-dimensional structure of a lacrimal gland organ.

DESCRIPTION OF EMBODIMENTS

<Method of Producing Lacrimal Gland Epithelial Cell>

A method of producing a lacrimal gland epithelial cell of the present invention (hereinafter sometimes referred to as "production method of the present invention") includes a step A including increasing expression of Pax6 gene in a pluripotent stem cell or transfecting PAX6 protein thereinto, and increasing expression of Foxc1 gene or Foxp1 gene in the pluripotent stem cell or transfecting FOXC1 protein or FOXP1 protein thereinto, and as necessary, further includes a step B of culturing the cell obtained in the step A in a keratinocyte (corneal epithelial cell) growth medium.

The term "medium" as used herein refers to one in a state obtained by adding water to "medium components" that allow cells to be cultured. Herein, the "Pax6 gene" and the "Foxc1 gene or Foxp1 gene", and preferably further the "Six1 gene" are sometimes collectively referred to as "genes in the present invention," and the "PAX6 protein" and the "FOXC1 protein or FOXP1 protein", and preferably further the "SIX1 protein" are sometimes collectively referred to as "proteins in the present invention."

Figure 3:
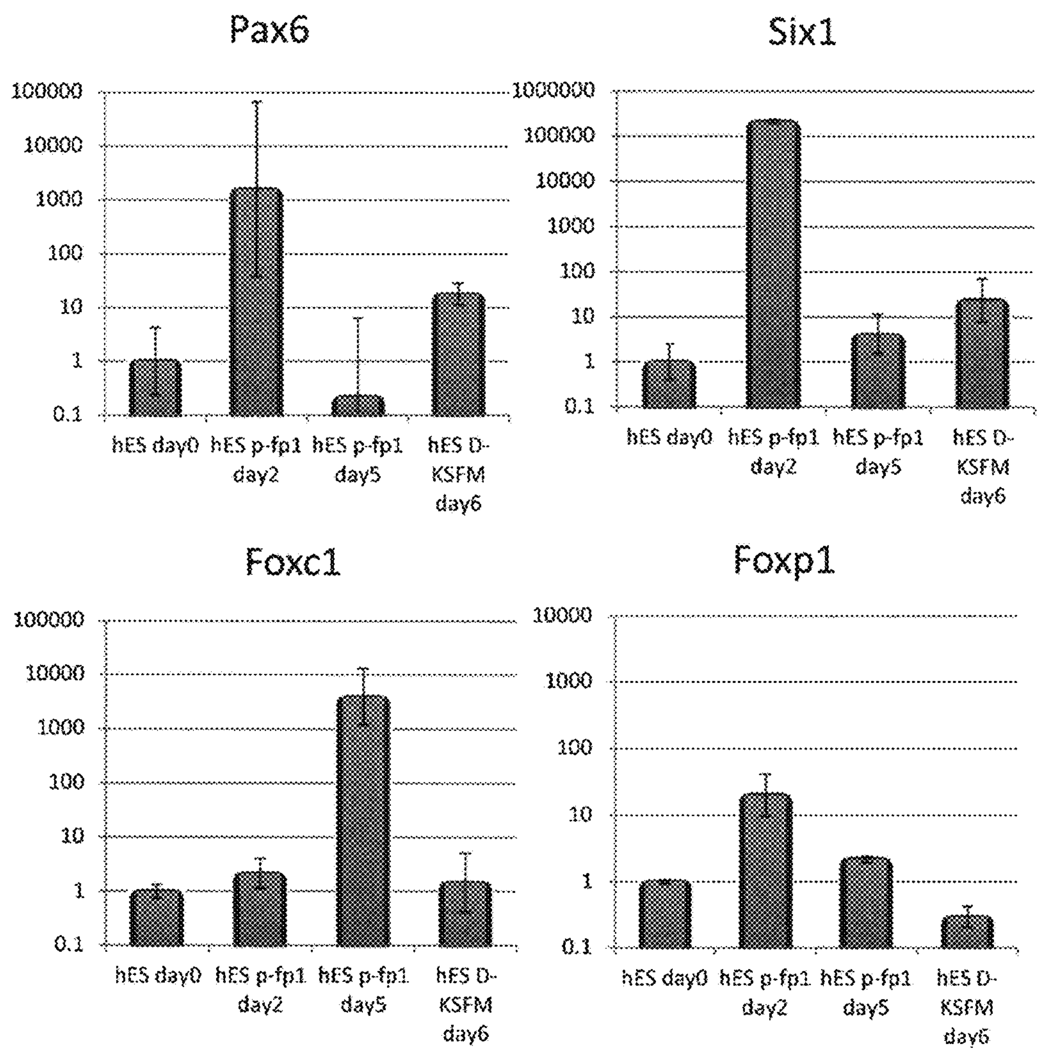
FIG. 3 are graphs for showing the results of measurement of the expression levels of lacrimal gland epithelial cell marker genes in cells in the case of transfecting the mRNAs of "Pax6 and Foxp1" into human ES cells, followed by culture in a keratinocyte growth medium. "hES p-fp1 day2" represents the results of cells on the 2nd day after the initiation of the transfection of the mRNAs, and "hES p-fp1 day5" represents the results of cells on the 5th day after the initiation of the transfection of the mRNAs. In addition, "hES day0" represents the results of cells on the day of the transfection of the mRNAs (1st day after the initiation of the culture) before the transfection of the mRNAs, and "hES DKSFM day6" represents the results of cells on day 6, the cells having been treated and cultured in the same manner except that the mRNAs were not transfected.

As apparent from results shown in FIG. 3, when the expression of the Foxp1 gene is increased in the pluripotent stem cell, the expression of the Foxc1 gene also increases. Therefore, in the step A, the expression of the Foxp1 gene may be increased in place of that of the Foxc1 gene or together with that of the Foxc1 gene, or the FOXP1 protein may be transfected in place of the FOXC1 protein or together with the FOXC1 protein.

The action mechanism of the present invention is not known in detail. However, it is considered that, when a state in which larger amounts of the PAX6 protein and the FOXC1 protein are present is achieved in the pluripotent stem cell, larger amounts of the above-mentioned two proteins act as transcription factors in the pluripotent stem cell to induce differentiation of the pluripotent stem cell into the lacrimal gland epithelial cell.

As a preferred mode of the step A, the following mode is given: the step A further includes increasing expression of the Six1 gene in the pluripotent stem cell or transfecting the SIX1 protein thereinto. As apparent from results shown in FIG. 1 and FIG. 3, in the pluripotent stem cell, when "the expression of the Pax6 gene is increased or the PAX6 protein is transfected," and "the expression of the Foxc1 gene or the Foxp1 gene is increased or the FOXC1 protein or the FOXP1 protein is transfected," the expression of the Six1 gene also increases. Therefore, the increase of the expression of the Six1 gene or the transfection of the SIX1 protein is not essential for the present invention, but is preferred because a morphological change into the lacrimal gland epithelial cell can be made more distinct, and thus the direction of differentiation into a lacrimal gland epithelial cell line can be made more distinct. The production method of the present invention may be a method of producing a lacrimal gland epithelial cell in vitro, and the step A and the step B may be performed in vitro.

In the production method of the present invention, "increasing expression of the genes in the present invention" means increasing the expression of the genes at protein level ultimately. When the expression of a gene at transcription level (mRNA level) is increased, its expression at protein level generally increases also, and hence an increase in expression of the genes in the present invention may be confirmed at protein level, or may be confirmed at transcription level (mRNA level).

The presence or absence, or degree of an increase in expression at protein level of the genes in the present invention may be confirmed by a known method, for example, an immunohistological staining method. A commercially available product may be used as a labelled antibody to be used in the immunohistological staining method, or the labelled antibody may be produced by a known method. In addition, the presence or absence, or degree of an increase at transcription level of the genes in the present invention may be confirmed by a known method, for example, quantitative RT-PCR. A person skilled in the art could appropriately design and produce the sequences of primers to be used in the quantitative RT-PCR on the basis of sequence information on a gene of interest. Sequence information on human Pax6 has an accession number of NM_000280.4, sequence information on human Foxc1 has an accession number of NM_001453.2, sequence information on human Foxp1 has an accession number of NM_032682.5, and sequence information on human Six1 has an accession number of NM_005982.3. In addition, preferred specific examples of a primer set designed on the basis of the above-mentioned sequence information may include primer sets having nucleotide sequences set forth in SEQ ID NOS: 9 and 10 (primer set for human Pax6), SEQ ID NOS: 11 and 12 (primer set for human Foxc1), SEQ ID NOS: 13 and 14 (primer set for human Foxp1), and SEQ ID NOS: 15 and 16 (primer set for human Six1).

Pax6 gene in the present invention is not particularly limited as long as the Pax6 gene is formed of any one of the following polynucleotides:

(a-1) a polynucleotide encoding a protein having an amino acid sequence set forth in SEQ ID NO: 2;

(b-1) a polynucleotide encoding a protein having an amino acid sequence having one or several amino acids deleted, substituted, and/or added in the amino acid sequence set forth in SEQ ID NO: 2, and having PAX6 activity;

(c-1) a polynucleotide encoding a protein having an amino acid sequence having at least 80% or more identity to the amino acid sequence set forth in SEQ ID NO: 2, and having PAX6 activity;

(d-1) a polynucleotide having a nucleotide sequence set forth in SEQ ID NO: 1;

(e-1) a polynucleotide that has a nucleotide sequence having one or several nucleotides deleted, substituted, and/or added in the nucleotide sequence set forth in SEQ ID NO: 1, and encodes a protein having PAX6 activity;

(f-1) a polynucleotide that has a nucleotide sequence having at least 80% or more identity to the nucleotide sequence set forth in SEQ ID NO: 1, and encodes a protein having PAX6 activity; and (g-1) a polynucleotide that hybridizes with a base sequence complementary to the nucleotide sequence set forth in SEQ ID NO: 1 under stringent conditions, and encodes a protein having PAX6 activity.

In addition, the PAX6 protein in the present invention is not particularly limited as long as the protein is any one of the following proteins:

(A-1) a protein having the amino acid sequence set forth in SEQ ID NO: 2;

(B-1) a protein having an amino acid sequence having one or several amino acids deleted, substituted, and/or added in the amino acid sequence set forth in SEQ ID NO: 2, and having PAX6 activity; and (C-1) a protein having an amino acid sequence having at least 80% or more identity to the amino acid sequence set forth in SEQ ID NO: 2, and having PAX6 activity.

In the foregoing, the "protein having PAX6 activity" means such a protein that, when the protein or a polynucleotide encoding the protein is transfected together with a polynucleotide encoding the FOXC1 protein, or together with the FOXP1 protein into pluripotent stem cells, and then the cells are cultured, lacrimal gland epithelial cells can be produced.

The above-mentioned SEQ ID NO: 1 sets forth the nucleotide sequence of cDNA of human Pax6 gene, and the above-mentioned SEQ ID NO: 2 sets forth the amino acid sequence of human PAX6 protein. Sequence data on Pax6 has already been known also in various vertebrates other than a human, and has been disclosed in public data banks, such as GenBank. For example, sequence data on the Pax6 gene and the PAX6 protein is disclosed in BC036957.1 for a mouse, in BC128741.1 for a rat, in EF141016.1 for a dog, in BC116038.1 for cattle, and in BC075551.1 for *Xenopus tropicalis*.

Foxc1 gene in the present invention is not particularly limited as long as the Foxc1 gene is formed of anyone of the following polynucleotides:

(a-2) a polynucleotide encoding a protein having an amino acid sequence set forth in SEQ ID NO: 4;

(b-2) a polynucleotide encoding a protein having an amino acid sequence which have one or several amino acids deleted, substituted, and/or added in the amino acid sequence set forth in SEQ ID NO: 4, and with FOXC1 activity;

(c-2) a polynucleotide encoding a protein having an amino acid sequence which have at least 80% or more identity to the amino acid sequence set forth in SEQ ID NO: 4, and with FOXC1 activity;

(d-2) a polynucleotide having a nucleotide sequence set forth in SEQ ID NO: 3;

(e-2) a polynucleotide that has a nucleotide sequence having one or several nucleotides deleted, substituted, and/or added in the nucleotide sequence set forth in SEQ ID NO: 3, and encodes a protein with FOXC1 activity;

(f-2) a polynucleotide that has a nucleotide sequence having at least 80% or more identity to the nucleotide sequence set forth in SEQ ID NO: 3, and encodes a protein with FOXC1 activity; and (g-2) a polynucleotide that hybridizes with a base sequence complementary to the nucleotide sequence set forth in SEQ ID NO: 3 under stringent conditions, and encodes a protein having FOXC1 activity.

In addition, the FOXC1 protein in the present invention is not particularly limited as long as the protein is any one of the following proteins:

(A-2) a protein having the amino acid sequence set forth in SEQ ID NO: 4;

(B-2) a protein having an amino acid sequence having one or several amino acids deleted, substituted, and/or added in the amino acid sequence set forth in SEQ ID NO: 4, and having FOXC1 activity; and (C-2) a protein having an amino acid sequence having at least 80% or more identity to the amino acid sequence set forth in SEQ ID NO: 4, and having FOXC1 activity.

In the foregoing, the "protein having FOXC1 activity" means such a protein that, when the protein or a polynucleotide encoding the protein is transfected together with a polynucleotide encoding the PAX6 protein, or together with the PAX6 protein into pluripotent stem cells, and then the cells are cultured in a medium, lacrimal gland epithelial cells can be produced.

The above-mentioned SEQ ID NO: 3 sets forth the nucleotide sequence of cDNA of human Foxc1 gene, and the above-mentioned SEQ ID NO: 4 sets forth the amino acid sequence of human FOXC1 protein. Sequence data on Foxc1 has already been known also in various vertebrates other than a human, and has been disclosed in public data banks, such as GenBank. For example, sequence data on the Foxc1 gene and the FOXC1 protein is disclosed in NM_008592.2 for a mouse, in NM_134338.1 for a rat, in NM_001088214.1 and NM_001096377.1 for *Xenopus laevis*, and in EU196406.1 for *Scyliorhinus canicula.*

Foxp1 gene in the present invention is not particularly limited as long as the Foxp1 gene is formed of any one of the following polynucleotides:

(a-3) a polynucleotide encoding a protein having an amino acid sequence set forth in SEQ ID NO: 6;

(b-3) a polynucleotide encoding a protein having an amino acid sequence having one or several amino acids deleted, substituted, and/or added in the amino acid sequence set forth in SEQ ID NO: 6, and having FOXP1 activity;

(c-3) a polynucleotide encoding a protein having an amino acid sequence having at least 80% or more identity to the amino acid sequence set forth in SEQ ID NO: 6, and having FOXP1 activity;

(d-3) a polynucleotide having a nucleotide sequence set forth in SEQ ID NO: 5;

(e-3) a polynucleotide that has a nucleotide sequence having one or several nucleotides deleted, substituted, and/or added in the nucleotide sequence set forth in SEQ ID NO: 5, and encodes a protein having FOXP1 activity;

(f-3) a polynucleotide that has a nucleotide sequence having at least 80% or more identity to the nucleotide sequence set forth in SEQ ID NO: 5, and encodes a protein having FOXP1 activity; and (g-3) a polynucleotide that hybridizes with a base sequence complementary to the nucleotide sequence set forth in SEQ ID NO: 5 under stringent conditions, and encodes a protein having FOXP1 activity.

In addition, the FOXP1 protein in the present invention is not particularly limited as long as the protein is any one of the following proteins:

(A-3) a protein having the amino acid sequence set forth in SEQ ID NO: 6;

(B-3) a protein having an amino acid sequence having one or several amino acids deleted, substituted, and/or added in the amino acid sequence set forth in SEQ ID NO: 6, and having FOXP1 activity; and (C-3) a protein having an amino acid sequence having at least 80% or more identity to the amino acid sequence set forth in SEQ ID NO: 6, and having FOXP1 activity.

In the foregoing, the "protein having FOXP1 activity" means such a protein that, when the protein or a polynucleotide encoding the protein is transfected together with a polynucleotide encoding the PAX6 protein, or together with the PAX6 protein into pluripotent stem cells, and then the cells are cultured in a medium, lacrimal gland epithelial cells can be produced.

The above-mentioned SEQ ID NO: 5 sets forth the nucleotide sequence of cDNA of human Foxp1 gene, and the above-mentioned SEQ ID NO: 6 sets forth the amino acid sequence of human FOXP1 protein. Sequence data on Foxp1 has already been known also in various vertebrates other than a human, and has been disclosed in public data banks, such as GenBank. For example, sequence data on the Foxp1 gene and the FOXP1 protein is disclosed in NM_053202.2 for a mouse, in NM_001034131.1 for a rat, and in NM_001095533.1 for *Xenopus laevis.*

Six1 gene in the present invention is not particularly limited as long as the Six1 gene is formed of any one of the following polynucleotides:

(a-4) a polynucleotide encoding a protein having an amino acid sequence set forth in SEQ ID NO: 8;

(b-4) a polynucleotide encoding a protein having an amino acid sequence having one or several amino acids deleted, substituted, and/or added in the amino acid sequence set forth in SEQ ID NO: 8, and having SIX1 activity;

(c-4) a polynucleotide encoding a protein having an amino acid sequence having at least 80% or more identity to the amino acid sequence set forth in SEQ ID NO: 8, and having SIX1 activity;

(d-4) a polynucleotide having a nucleotide sequence set forth in SEQ ID NO: 7;

(e-4) a polynucleotide that has a nucleotide sequence having one or several nucleotides deleted, substituted, and/or added in the nucleotide sequence set forth in SEQ ID NO: 7, and encodes a protein having SIX1 activity;

(f-4) a polynucleotide that has a nucleotide sequence having at least 80% or more identity to the nucleotide sequence set forth in SEQ ID NO: 7, and encodes a protein having SIX1 activity; and (g-4) a polynucleotide that hybridizes with a base sequence complementary to the nucleotide sequence set forth in SEQ ID NO: 7 under stringent conditions, and encodes a protein having SIX1 activity.

In addition, the SIX1 protein in the present invention is not particularly limited as long as the protein is any one of the following proteins:

(A-4) a protein having the amino acid sequence set forth in SEQ ID NO: 8;

(B-4) a protein having an amino acid sequence having one or several amino acids deleted, substituted, and/or added in the amino acid sequence set forth in SEQ ID NO: 8, and having SIX1 activity; and (C-4) a protein having an amino acid sequence having at least 80% or more identity to the amino acid sequence set forth in SEQ ID NO: 8, and having SIX1 activity.

In the foregoing, the "protein having SIX1 activity" means such a protein (P) that, when a case in which the protein (P) or a polynucleotide encoding the protein (P) is transfected into pluripotent stem cells together with a polynucleotide encoding the PAX6 protein, or the PAX6 protein, and a polynucleotide encoding the FOXC1 protein, or the FOXC1 protein, and then the cells are cultured in a medium (case A), and a case in which the polynucleotide encoding the PAX6 protein, or the PAX6 protein, and the polynucleotide encoding the FOXC1 protein, or the FOXC1 protein are transfected into pluripotent stem cells, and then the cells are cultured in a medium (case B) are compared to each other, the expression amount of Barx2 gene at mRNA level is higher and a morphological change into lacrimal gland epithelial cells is more distinct in the case A.

The "stringent conditions" refers to conditions under which only specific hybridization occurs and non-specific hybridization does not occur. Such conditions are generally conditions such as hybridization in a buffer containing 5×SSC and 1% SDS at 37° C. and washing treatment with a buffer containing 1×SSC and 0.1% SDS at 37° C., preferably conditions such as hybridization in a buffer containing 5×SSC and 1% SDS at 42° C. and washing treatment with a buffer containing 0.5×SSC and 0.1% SDS at 42° C., more preferably conditions such as hybridization in a buffer containing 5×SSC and 1% SDS at 65° C. and washing treatment with a buffer containing 0.2×SSC and 0.1% SDS at 65° C. Whether or not DNA obtained by utilizing hybridization encodes a polypeptide having activity may be found out by, for example, transfecting the DNA into *Escherichia coli* or the like to cause expression, and investigating whether or not the *Escherichia coli* or the like can generate a protein of interest. DNAs obtained by hybridization generally have high identity to respective genes. The high identity refers to 90% or more identity, preferably 95% or more identity, more preferably 98% or more identity.

The above-mentioned SEQ ID NO: 7 sets forth the nucleotide sequence of cDNA of human Six1 gene, and the above-mentioned SEQ ID NO: 8 sets forth the amino acid sequence of human SIX1 protein. Sequence data on Six1 has already been known also in various vertebrates other than a human, and has been disclosed in public data banks, such as GenBank. For example, sequence data on the Six1 gene and the SIX1 protein is disclosed in NM_009189.3 for a mouse, in NM_053759.1 for a rat, in KF381338.1 for a dog, and in BC169929.1 for *Xenopus laevis.*

The above-mentioned "amino acid sequence having one or several amino acids deleted, substituted, and/or added" means an amino acid sequence having the following number of amino acids deleted, substitute, or added. The number of amino acids falls within, for example, the range of from 1 to 30, preferably the range of from 1 to 20, more preferably the range of from 1 to 15, still more preferably the range of from 1 to 10, even more preferably the range of from 1 to 5, still even more preferably the range of from 1 to 3, yet still more preferably the range of from 1 to 2. The above-mentioned "nucleotide sequence having one or several nucleotides deleted, substituted, and/or added" means a nucleotide sequence having the following number of nucleotides deleted, substituted, and/or added. The number of nucleotides falls within, for example, the range of from 1 to 40, preferably the range of from 1 to 30, more preferably the range of from 1 to 20, still more preferably the range of from 1 to 15, even more preferably the range of from 1 to 10, still even more preferably the range of from 1 to 5, yet still more preferably the range of from 1 to 3, yet even more preferably the range of from 1 to 2.

For example, a polynucleotide having such nucleotide sequence having one or several nucleotides deleted, substituted, and/or added (mutant polynucleotide) may be produced by any method known to a person skilled in the art, such as chemical synthesis, a genetic engineering technique, or mutagenesis. Specifically, the mutant polynucleotide may be acquired by introducing a mutation into the polynucleotide having the nucleotide sequence set forth in SEQ ID NO: 1, 3, 5, or 7 through use of, for example, a method involving subjecting the polynucleotide to the action of a mutagenic agent through contact therewith, a method involving irradiating the polynucleotide with ultraviolet light, or a genetic engineering technique. A site-directed mutagenesis method, which is one of the genetic engineering techniques, is useful because the method allows a specific mutation to be introduced at a specific position. The site-directed mutagenesis method may be performed in conformity to a method disclosed in, for example, Molecular Cloning: A laboratory Mannual, 2nd Ed., Cold Spring Harbor Laboratory, Cold Spring Harbor, N.Y., 1989. (hereinafter abbreviated as "Molecular Cloning, 2nd Ed."), or Current Protocols in Molecular Biology, Supplement 1 to 38, John Wiley & Sons (1987-1997). Through expression of the mutant polynucleotide by use of an appropriate expression system, a protein having an amino acid sequence having one or several amino acids deleted, substituted, and/or added can be obtained.

The above-mentioned "nucleotide sequence having at least 80% or more identity to the nucleotide sequence set forth in SEQ ID NO: 1, 3, 5, or 7" is not particularly limited as long as respective identity to the nucleotide sequence set forth in SEQ ID NO: 1, 3, 5, or 7 is 80% or more, and the following case is included: the identity is preferably 85% or more, more preferably 88% or more, still more preferably 90% or more, even more preferably 93% or more, particularly preferably 95% or more, most preferably 98% or more.

The above-mentioned "amino acid sequence having at least 80% or more identity to the amino acid sequence set forth in SEQ ID NO: 2, 4, 6, or 8" is not particularly limited as long as respective identity to the amino acid sequence set forth in SEQ ID NO: 2, 4, 6, or 8 is 80% or more, and the following case is included: the identity is preferably 85% or more, more preferably 88% or more, still more preferably 90% or more, even more preferably 93% or more, particularly preferably 95% or more, most preferably 98% or more.

A method of acquiring or method of preparing the genes in the present invention described above is not particularly limited. The genes in the present invention may be prepared by chemical synthesis in accordance with a conventional method as well as a method involving: synthesizing appropriate oligonucleotides as probes or primers on the basis of sequence information on the genes in the present invention of a human (Pax6 gene: SEQ ID NO: 1; Foxc1 gene: SEQ ID NO: 3; Foxp1 gene: SEQ ID NO: 5; Six1 gene: SEQ ID NO: 7), or known sequence information on those genes of any other biological species; and cloning cDNAs of the genes in the present invention of a vertebrate, such as a human, from mRNAs, cDNAs or a cDNA library derived from cells or tissues of the vertebrate, such as a human, through use of a hybridization method or a (RT-) PCR method (e.g., a method disclosed in Molecular Cloning, 2nd Ed.), to thereby acquire the genes in the present invention of the vertebrate, such as a human. In addition, by, for example, a hybridization method involving using the acquired genes in the present invention or part of those genes as probes, the genes in the present invention may also be acquired from a vertebrate of a kind different from the vertebrate from which those genes in the present invention are derived.

A method of acquiring or method of preparing the proteins in the present invention described above is not particularly limited. The proteins in the present invention may be any of proteins of natural origin, chemically synthesized proteins, and recombinant proteins produced by a gene recombination technology. When the proteins of natural origin are acquired, the proteins in the present invention may be acquired from cells or tissues expressing such proteins by appropriately combining methods of isolating and purifying proteins.

The protein having an amino acid sequence having one or several amino acids deleted, substituted, and/or added in the amino acid sequence set forth in SEQ ID NO: 2, 4, 6 or 8, or the protein having an amino acid sequence having 80% or more identity to the amino acid sequence set forth in SEQ ID NO: 2, 4, 6, or 8 could appropriately be prepared or acquired by a person skilled in the art on the basis of sequence information on the proteins in the present invention of a human (SEQ ID NO: 2, 4, 6, or 8), sequence information on the genes in the present invention of a human (SEQ ID NO: 1, 3, 5, or 7), or known sequence information on those proteins or genes of any other biological species. For example, polynucleotides encoding the proteins in the present invention of a vertebrate, such as a human, may be acquired by: synthesizing appropriate oligonucleotides as probes or primers on the basis of sequence information on human Pax6 (SEQ ID NO: 1 or 2), Foxc1 (SEQ ID NO: 3 or 4), Foxp1 (SEQ ID NO: 5 or 6), or Six1 (SEQ ID NO: 7 or 8), or known sequence information on those proteins or genes of any other biological species; and cloning cDNAs of the genes in the present invention of the vertebrate, such as a human, from mRNAs, cDNAs or a cDNA library derived from cells or tissues of the vertebrate, such as a human, through use of a hybridization method or a (RT-)PCR method (e.g., a method disclosed in Molecular Cloning, 2nd Ed.). In addition, by, for example, a hybridization method involving using such polynucleotides as probes, the polynucleotides encoding the proteins in the present invention may also be acquired from a vertebrate of a kind different from the vertebrate from which those polynucleotides are derived. The proteins in the present invention derived from a vertebrate, such as a human, may be acquired by incorporating the thus obtained polynucleotides encoding the proteins in the present invention into expression vectors, transfecting the expression vectors into appropriate host cells, culturing the cells, and collecting recombinant proteins from the cultured cells or their conditioned medium.

A method of increasing the expression of the genes in the present invention in the pluripotent stem cell in the step A is not particularly limited, and may be a method involving increasing the expression of the genes in the present invention without transfecting polynucleotides encoding the proteins in the present invention into the pluripotent stem cell. However, a suitable example may be a method involving transfecting the polynucleotides encoding the proteins in the present invention into the pluripotent stem cell. Each of such polynucleotides may be DNA or RNA, may be a single strand or double strands, and may be linear or circular, and examples thereof may include genomic DNAs, cDNAs, mRNAs, and polynucleotides containing the foregoing, which encode the proteins in the present invention. Although SEQ ID NOS: 1, 3, 5, and 7 are described as DNA sequences, when the polynucleotides of the present invention are RNAs, T in each of the nucleotide sequences of the above-mentioned SEQ ID NOS represents U. Examples of the polynucleotides encoding the proteins in the present invention may include “expression vectors containing the polynucleotides encoding the proteins in the present invention” (hereinafter sometimes referred to as “expression vectors in the present invention”) and “mRNAs encoding the proteins in the present invention” (hereinafter sometimes referred to as “mRNAs in the present invention”). Of those, a preferred example may be “mRNAs in the present invention” because of higher safety in clinical application. When the “mRNAs in the present invention” are transfected into the pluripotent stem cell, the mRNAs are directly translated into the proteins in the present invention, and hence there is no fear of incorporation of the polynucleotides of the genes in the present invention increased in expression onto the genome of the pluripotent stem cell.

As mRNA encoding the PAX6 protein, there may be given a polyribonucleotide obtained by adding a polyA sequence to the 3' end of any one polynucleotide selected from the group consisting of the polynucleotides described in the above-mentioned (a-1) to (g-1). As mRNA encoding the FOXC1 protein, there may be given a polyribonucleotide obtained by adding a polyA sequence to the 3' end of any one polynucleotide selected from the group consisting of the polynucleotides described in the above-mentioned (a-2) to (g-2). As mRNA encoding the FOXP1 protein, there may be given a polyribonucleotide obtained by adding a polyA sequence to the 3' end of anyone polynucleotide selected from the group consisting of the polynucleotides described in the above-mentioned (a-3) to (g-3). As mRNA encoding the SIX1 protein, there may be given a polyribonucleotide obtained by adding a polyA sequence to the 3' end of any one polynucleotide selected from the group consisting of the polynucleotides described in the above-mentioned (a-4) to (g-4). The number of nucleotides of the polyA sequence is not particularly limited as long as, when the polyribonucleotide is transfected into the pluripotent stem cell, the polyribonucleotide can be translated into the protein encoded therein. The number of nucleotides of the polyA sequence may fall within, for example, the range of from 30 to 300, preferably the range of from 50 to 250.

The mRNAs in the present invention each preferably have a cap structure at its 5' end from the viewpoint of obtaining higher translation efficiency in cells having transfected therein the mRNAs. A preferred example of such cap structure may be 7-methylguanosine.

The mRNAs in the present invention may be produced by a conventional method on the basis of sequence information on the genes in the present invention. For example, the mRNAs in the present invention may be produced by chemical synthesis, or may be produced by in vitro transcription. The in vitro transcription may be performed, for example, by a conventional method with use of the expression vectors in the present invention and a commercially available kit for an in vitro transcription reaction.

A method of transfecting the polynucleotides encoding the proteins in the present invention (e.g., “expression vectors in the present invention” or “mRNAs in the present invention”) into the pluripotent stem cell is not particularly limited as long as the method can transfect the polynucleotides into the pluripotent stem cell. Examples thereof may include a lipofection method, a liposome method, an electroporation method, a calcium phosphate coprecipitation method, a diethylaminoethyl (DEAE)-dextran method, a microinjection method, and a gene gun method. Of those, a lipofection method is a preferred example because of its simple operation and high transfection efficiency of polynucleotides. Transfection using the lipofection method may be performed by using a commercially available reagent, for example, Lipofectamine (registered trademark in Japan) (manufactured by Life Technologies) or LipoTAXI (registered trademark in Japan) (manufactured by Agilent Technologies) in accordance with its attached instruction manual. In the transfection of a polynucleotide into the pluripotent stem cell using the lipofection method, the length of time for which the polynucleotide and the pluripotent stem cell are brought into contact with each other may fall within, for example, the range of from 0.5 hour to 4 hours, preferably the range of from 1 hour to 3.5 hours, more preferably the range of from 1.5 hours to 3 hours.

When the expression vectors in the present invention are viral vectors, the following may be performed: plasmids containing the polynucleotides encoding the proteins in the present invention are transfected into appropriate packaging cells (e.g., HEK293T cells), viral vectors produced in a culture supernatant are collected, and the pluripotent stem cell is infected with the vectors by a method appropriate for each viral vector. For example, for specific means in the case of using lentiviral vectors as the vectors, reference may be made to Science, 318, 1917-1920 (2007) and the like. For the case of using retroviral vectors, reference may be made to WO 2007/69666, Cell, 126, 663-676 (2006), Cell, 131, 861-872 (2007), and the like. For the case of using adenoviral vectors, reference may be made to Science, 322, 945-949 (2008).

As described above, in the production method of the present invention, the expression of the genes in the present invention may be increased in the pluripotent stem cell, or the proteins in the present invention may be transfected into the pluripotent stem cell. In addition, it is possible to increase the expression of some kinds of genes out of the genes in the present invention in the pluripotent stem cell, and transfect the protein corresponding to the remaining kind of gene into the pluripotent stem cell, or it is possible to increase gene expression in the pluripotent stem cell for some or all kinds of genes out of the genes in the present invention, and transfect the proteins corresponding to those genes into the pluripotent stem cell.

A method of transfecting the proteins in the present invention into the pluripotent stem cell is not particularly limited as long as the method can transfect the proteins in the present invention into the pluripotent stem cell. Examples thereof may include a method involving using a protein transfection reagent, a method involving using a protein transduction domain (PTD)—or cell penetrating peptide (CPP)—fused protein, and a microinjection method. As commercially available products of the protein transfection reagent, there are given, for example: cationic lipid-based protein transfection reagents, such as BioPORTER Protein Delivery Reagent (manufactured by Gene Therapy Systems), Pro-Ject™ Protein Transfection Reagent (manufactured by PIERCE), and ProVectin (manufactured by IMGENEX); lipid-based protein transfection reagents, such as Profect-1 (manufactured by Targeting Systems); membrane-permeable peptide-based protein transfection reagents, such as Penetratin Peptide (manufactured by Q-biogene) and Chariot Kit (manufactured by Active Motif); and GenomONE (manufactured by Ishihara Sangyo Kaisha, Ltd.) utilizing HVJ envelope (inactivated Sendai virus). The transfection may be performed in accordance with the protocol attached to each of those reagents, and a general procedure may involve: diluting each of the proteins in the present invention in an appropriate solvent (e.g., a buffer, such as PBS or HEPES), adding a transfection reagent, incubating the resultant at room temperature for from about 5 minutes to about 15 minutes to form a complex, adding the complex to cells exchanged to a serum-free medium, and incubating the cells at 37° C. for from 1 hour to several hours.

The above-mentioned microinjection is a method involving loading a glass needle having a tip diameter of about 1 μm with a protein solution and transfecting the protein into cells by puncture, and can reliably transfect the protein into the cells.

In the production method of the present invention, the degree to which the expression of the genes in the present invention is increased is not particularly limited as long as the lacrimal gland epithelial cell can be produced from the pluripotent stem cell. The degree may be, for example, as follows: a transcription level (mRNA level) and/or a protein level reaches 10 or more times (e.g., 10 or more times and less than 50 times) that before the increase at least by a certain time point (preferably within 5 days from when the pluripotent stem cell is subjected to the operation of increasing the expression) at least once. As long as the lacrimal gland epithelial cell can be produced from the pluripotent stem cell, the degree to which the expression of the genes in the present invention is increased may be the same or different for each of the genes in the present invention. In terms of transcription level (mRNA level) and/or protein level, the ratio "Pax6 gene:Foxp1 gene" may fall within, for example, the range of from 1.0:0.1 to 0.1:1.0, preferably the range of from 1.0:0.5 to 0.5:1.0, more preferably the range of from 1:0.8 to 0.8:1.0. In addition, when the expression of the Six1 gene is also increased, the ratio "Pax6 gene:Six1 gene" in degree of increase in expression may fall within, for example, the range of from 1.0:0.1 to 0.1:1.0, preferably the range of from 1.0:0.5 to 0.5:1.0, more preferably the range of from 1.0:0.8 to 0.8:1.0. In addition, when the expression of the Foxp1 gene is increased in place of the Foxc1 gene or together with the Foxc1 gene, the ratio "Pax6 gene:Foxp1 gene" in degree of increase in expression may fall within, for example, the range of from 1.0:0.1 to 0.1:1.0, preferably the range of from 1.0:0.5 to 0.5:1.0, more preferably the range of from 1.0:0.8 to 0.8:1.0.

The transfection amount of the proteins in the present invention, or the polynucleotides encoding the proteins in the present invention into the pluripotent stem cell is not particularly limited as long as the lacrimal gland epithelial cell can be produced from the pluripotent stem cell. The transfection amount of the proteins in the present invention may fall within, for example, the range of from 0.001 pg to 100 ng per one kind of the proteins in the present invention with respect to one cell of the pluripotent stem cell. The transfection amount of the polynucleotides encoding the proteins in the present invention, which varies depending on whether or not an expression vector is included, and also on the mode of each polynucleotide, such as a single strand or double strands, may fall within, for example, the range of from 0.5 pg to 50 ng, preferably the range of from 5 pg to 10 ng per one kind of the polynucleotides with respect to one cell of the pluripotent stem cell. In addition, when the polynucleotides encoding the proteins in the present invention are mRNAs, the transfection amount may fall within, for example, the range of from 0.1 pg to 10 ng, preferably the range of from 1 pg to 1 ng, more preferably the range of from 3 pg to 300 pg per one kind of the mRNAs with respect to one cell of the pluripotent stem cell.

As long as the lacrimal gland epithelial cell can be produced from the pluripotent stem cell, the transfection amount of the proteins in the present invention may be the same or different for each kind of the proteins in the present invention. The ratio "PAX6 protein: FOXC1 protein" in terms of weight ratio may fall within, for example, the range of from 1.0:0.1 to 0.1:1.0, preferably the range of from 1.0:0.5 to 0.5:1.0, more preferably the range of from 1:0.8 to 0.8:1.0. In addition, when the SIX1 protein is also transfected, the transfection ratio "PAX6 protein:SIX1 protein" in terms of weight ratio may fall within, for example, the range of from 1.0:0.1 to 0.1:1.0, preferably the range of from 1.0:0.5 to 0.5:1.0, more preferably the range of from 1:0.8 to 0.8:1.0. In addition, when the FOXP1 protein is transfected in place of the FOXC1 protein or together with the FOXC1 protein, the transfection ratio "PAX6 protein: FOXP1 protein" in terms of weight ratio may fall within, for example, the range of from 1.0:0.1 to 0.1:1.0, preferably the range of from 1.0:0.5 to 0.5:1.0, more preferably the range of from 1:0.8 to 0.8:1.0.

As long as the lacrimal gland epithelial cell can be produced from the pluripotent stem cell, the transfection amount of the polynucleotides encoding the proteins in the present invention may be the same or different for each kind of the polynucleotides. The ratio "Pax6:Foxc1" in terms of weight ratio may fall within, for example, the range of from 1.0:0.1 to 0.1:1.0, preferably the range of from 1.0:0.5 to 0.5:1.0, more preferably the range of from 1:0.8 to 0.8:1.0. In addition, when the polynucleotide encoding the SIX1 protein is also transfected, the ratio "Pax6:Six1" in terms of weight ratio may fall within, for example, the range of from 1.0:0.1 to 0.1:1.0, preferably the range of from 1.0:0.5 to 0.5:1.0, more preferably the range of from 1:0.8 to 0.8:1.0. In addition, when the polynucleotide encoding the FOXP1 protein is transfected in place of the polynucleotide encoding the FOXC1 protein or together with the polynucleotide encoding the FOXC1 protein, the transfection ratio "Pax6:

Foxp1" in terms of weight ratio may fall within, for example, the range of from 1.0:0.1 to 0.1:1.0, preferably the range of from 1.0:0.5 to 0.5:1.0, more preferably the range of from 1:0.8 to 0.8:1.0.

When the polynucleotides encoding the proteins in the present invention, or the proteins in the present invention are transfected into the pluripotent stem cell, the respective polynucleotides or the respective proteins may be transfected into the pluripotent stem cell simultaneously or sequentially, and the transfection may be performed simultaneously for part thereof and sequentially for the remaining other(s). When the transfection is sequential, the order of transfection is not particularly limited as long as the lacrimal gland epithelial cell can be produced from the pluripotent stem cell, but the following order is preferred:

[1] "the polynucleotide encoding the PAX6 protein, or the PAX6 protein"; and

[2] "the polynucleotide encoding the FOXC1 protein or the FOXP1 protein, or the FOXC1 protein or the FOXP1 protein."

In addition, when

[3] "the polynucleotide encoding the SIX1 protein, or the SIX1 protein" is further sequentially transfected, the [3] may be transfected, for example, between the [1] and [2], after the [2], simultaneously with the [1], or simultaneously with the [2].

The period of time between the transfection of the [1] and the transfection of the [2] is preferably within from 1 hour to 24 hours, more preferably within from 1 hour to 10 hours, still more preferably within from 1 hour to 5 hours. In addition, when the [3] is transfected, the period of time between the transfection of the [1] and the transfection of the [3] is preferably within from 1 hour to 24 hours, more preferably within from 1 hour to 10 hours, still more preferably within from 1 hour to 5 hours. In addition, when the [3] is transfected, the period of time between the transfection of the [2] and the transfection of the [3] is preferably within from 1 hour to 24 hours, more preferably within from 1 hour to 10 hours, still more preferably within from 1 hour to 5 hours, even more preferably within from 1 hour to 3 hours.

When the polynucleotides encoding the proteins in the present invention, or the proteins in the present invention are transfected into the pluripotent stem cell, the number of times of transfection of each polynucleotide or each protein into the pluripotent stem cell is not particularly limited as long as the lacrimal gland epithelial cell can be produced from the pluripotent stem cell. The number of times may be 1 for each polynucleotide or each protein, but may be set to 2 or more (preferably from 2 to 4, more preferably 2 or 3, still more preferably 2) for any or all of the polynucleotides to be transfected, or any or all of the proteins to be transfected. The setting of the number of times of transfection of each polynucleotide or each protein to 2 or more as described above is sometimes preferred particularly in the case of transfecting mRNAs or proteins. Unlike the case of transfecting the expression vectors in the present invention, in the case of transfecting the mRNAs in the present invention or the proteins in the present invention, most of the proteins generated from the mRNAs, or the transfected proteins disappear from the cell in about 24 hours from the transfection, and hence in order to produce the lacrimal gland epithelial cell from the pluripotent stem cell, it is sometimes preferred to perform the transfection 2 or more times.

When the mRNAs in the present invention or the proteins in the present invention are transfected, there may be preferably given a mode in which, for each mRNA or each protein, the same kind of mRNA or the same kind of protein is transfected every 12 hours to 36 hours (preferably every 18 hours to 30 hours) 2 or more times (preferably from 2 times to 4 times, more preferably 2 times or 3 times, still more preferably 2 times).

As a suitable mode of the case of sequentially transfecting the mRNAs in the present invention or the proteins in the present invention, there may be given, for example, a mode in which a step of transfecting "the polynucleotide encoding the FOXC1 protein or the FOXP1 protein, or the FOXC1 protein or the FOXP1 protein" and preferably further "the polynucleotide encoding the SIX1 protein, or the SIX1 protein" within from 1 hour to 10 hours (preferably within from 1 hour to 5 hours) from the transfection of "the polynucleotide encoding the PAX6 protein, or the PAX6 protein" is repeated within from 12 hours to 36 hours (preferably within from 18 hours to 30 hours).

When the expression of the genes in the present invention is increased, or the proteins in the present invention are transfected in the step A, medium components other than components particularly needed for a method for the increase or a method for the transfection are not particularly limited, and for example, a commercially available pluripotent stem cell growth medium may be used. Examples of such pluripotent stem cell growth medium may include STEM FIT (registered trademark in Japan) (manufactured by Ajinomoto Co., Inc.), Essential 8™ Medium (manufactured by Life Technologies), and HyCell-STEM™ Media (manufactured by GE Healthcare). From the viewpoint of growing the pluripotent stem cell more efficiently, a preferred example of the pluripotent stem cell growth medium may be a pluripotent stem cell growth medium supplemented with or containing a Rho-associated coiled-coil forming kinase/Rho-binding kinase (ROCK) inhibitor, such as Y27632, and/or B18R protein, a more preferred example may be a pluripotent stem cell growth medium supplemented with or containing a ROCK inhibitor, such as Y27632, and B18R protein, and a still more preferred example may be STEM FIT (registered trademark in Japan) (manufactured by Ajinomoto Co., Inc.) supplemented with Y27632 and B18R protein. The pluripotent stem cell growth medium and mediums given as suitable modes thereof described in this paragraph may be suitably used also when the pluripotent stem cell is cultured before the expression of the genes in the present invention is increased or the proteins in the present invention are transfected in the step A.

The ROCK inhibitor, such as Y27632, is known to have activity of suppressing cell death at the time of cell dissociation of pluripotent stem cells, and activity of maintaining an undifferentiated state of pluripotent stem cells for a longer period of time, and is often added to a pluripotent stem cell growth medium. The concentration of the ROCK inhibitor, such as Y27632, in the medium to be used in the step A may fall within, for example, the range of from 0.1 μM to 1,000 μM, preferably the range of from 1 μM to 100 μM, more preferably the range of from 5 μM to 20 μM. As the ROCK inhibitor, such as Y27632, a commercially available one may be used, and for example, Y27632 (manufactured by Wako Pure Chemical Industries, Ltd.) may be used.

The B18R protein is a protein having activity of potently neutralizing type I interferons, and is known to suppress cell death after the transfection of a polynucleotide or a protein. The concentration of the B18R protein in the medium to be used in the step A may fall within, for example, the range of from 2.5 ng/mL to 25 μg/mL, preferably the range of from 25 ng/mL to 2.5 μg/mL, more preferably the range of from 0.125 μg/mL to 0.5 μg/mL. As the B18R protein, a commercially available one may be used, and for example, one manufactured by Affymetrix Japan K.K. may be used.

When the cell is cultured in the production method of the present invention, a culture dish (Nunc, Corning, or the like) to be generally used in the culture of pluripotent stem cells may be used. A preferred example of such culture dish may be a culture dish coated with an extracellular matrix. Examples of the extracellular matrix may include laminin, collagen, fibronectin, and a combination thereof.

The kind of the pluripotent stem cell to be used in the production method of the present invention is not particularly limited as long as the cell allows the production of the lacrimal gland epithelial cell by the production method of the present invention. Suitable examples thereof may include ES cells and iPS cells. A biological species from which the pluripotent stem cell is derived is not particularly limited as long as the biological species is a vertebrate. Examples of the vertebrate include mammals, birds, reptiles, amphibians, and fish. Of those, preferred examples may be mammals, such as a human, a mouse, a rat, a guinea pig, a rabbit, a cat, a dog, a horse, cattle, a monkey, sheep, a goat, and a pig, and of those, a particularly preferred example may be a human.

The ES cells or the iPS cells to be used in the production method of the present invention may be obtained from the RIKEN Bioresource Center CELL BANK, the JCRB Cell Bank of the National Institute of Biomedical Innovation, or the like. In addition, the ES cells or the iPS cells may be produced. A method of producing the ES cells is not particularly limited, and a currently known production method may be used, or a method to be newly developed in the future may be used. For example, the ES cells may be established by removing an inner cell mass from the blastocyst of a fertilized egg of a vertebrate of interest and culturing the inner cell mass on a fibroblast feeder. A method of producing the iPS cells is also not particularly limited, and a currently known production method (JP 2009/075119 A1, JP 2011-529329 A, JP 2011-529330 A, JP 2012-507258 A, JP 2013-501505 A, JP 2013-519371 A, or JP 2013-544069 A) may be used, or a production method to be newly developed in the future may be used.

The production method of the present invention preferably includes the step B of culturing the cell obtained in the step A in a medium. When the cell obtained in the step A is cultured in, for example, a keratinocyte (corneal epithelial cell) growth medium, the lacrimal gland epithelial cell can be produced.

The keratinocyte growth medium means a medium capable of growing and maintaining keratinocytes, but as a matter of convenience, encompasses any and every medium capable of allowing the lacrimal gland epithelial cell to be produced when the cell obtained in the step A is cultured therein. A preferred example of such keratinocyte growth medium may be a medium obtained by adding a supplement to a keratinocyte basal medium capable of allowing keratinocytes to survive for a certain period of time. Preferred examples of such supplement may include epidermal growth factor (EGF) and cholera toxin. As the epidermal growth factor and the cholera toxin, commercially available ones may be used, and for example, ones manufactured by PeproTech and manufactured by List Biological Laboratories may be used, respectively. The use concentration of the epidermal growth factor is not particularly limited as long as the lacrimal gland epithelial cell can be produced. The use concentration of the epidermal growth factor may fall within, for example, the range of from 0.1 ng/mL to 1,000 ng/mL, preferably the range of from 1 ng/mL to 100 ng/mL, more preferably the range of from 5 ng/mL to 20 ng/mL. In addition, the use concentration of the cholera toxin is not particularly limited as long as the lacrimal gland epithelial cell can be produced. The use concentration of the cholera toxin may fall within, for example, the range of from 1 μg/mL to 10 mg/mL, preferably the range of from 10 μg/mL to 1 mg/mL, more preferably the range of from 50 μg/mL to 200 μg/mL.

In addition, from the viewpoint of obtaining better production efficiency of the lacrimal gland epithelial cell, the upper limit of the calcium concentration of the keratinocyte growth medium in the present invention is preferably 0.15 mM or less, more preferably 0.10 mM or less. In addition, the calcium concentration may be 0 mM, but is preferably 0.03 mM or more.

The above-mentioned keratinocyte basal medium means a medium capable of allowing keratinocytes to survive for a certain period of time, but as a matter of convenience, encompasses any and every medium capable of allowing, when the cell obtained in the step A is cultured therein, such cell to survive for a certain period of time. Such keratinocyte basal medium preferably contains, for example, one or two or more kinds of sugar (s), one or two or more kinds of inorganic salt (s), one or two or more kinds of amino acid (s), one or two or more kinds of vitamin (s), and one or two or more kinds of other components.

Specific examples of the sugars include: monosaccharides, such as glucose, mannose, fructose, and galactose; and disaccharides, such as sucrose, maltose, and lactose. Of those, glucose is particularly preferred. Those sugars may be added alone or in combination thereof.

Specific examples of the inorganic salts may include one kind or two or more kinds of inorganic salt (s) selected from calcium chloride, calcium nitrate, copper sulfate pentahydrate, iron (III) nitrate nonahydrate, iron (II) sulfate heptahydrate, magnesium chloride hexahydrate, magnesium sulfate, potassium chloride, sodium chloride, sodium bicarbonate, disodium hydrogen phosphate, disodium hydrogen phosphate dihydrate, sodium dihydrogen phosphate, sodium dihydrogen phosphate monohydrate, sodium dihydrogen phosphate dihydrate, sodium selenite pentahydrate, and zinc sulfate heptahydrate, and any inorganic salts or combination thereof may be used as long as the component advantageously acts on the production of the lacrimal gland epithelial cell from the pluripotent stem cell.

Specific examples of the amino acids may include one kind or two or more kinds of amino acid (s) selected from alanine, arginine, asparagine, aspartic acid, cystine, cysteine, glutamine, glycine, histidine, glutamic acid, hydroxyproline, isoleucine, leucine, lysine, methionine, phenylalanine, proline, serine, threonine, tryptophan, tyrosine, and valine, preferably L-form amino acids, and derivatives thereof and salts thereof, and derived products, such as hydrates, thereof.

Specific examples of the vitamins may include one kind or two or more kinds of vitamin (s) selected from biotin, choline, folic acid, inositol, niacin, pantothenic acid, pyridoxine, riboflavin, thiamine, vitamin B12, p-aminobenzoic acid (PABA), and ascorbic acid, and derivatives of these components and salts thereof, and derived products, such as hydrates, thereof.

Examples of the above-mentioned other components may include: buffering agents, such as HEPES; nucleic acids, such as nucleotides; pyruvic acid, and derivatives thereof and salts thereof, and derived products, such as hydrates, thereof; and phenol red. Preferred examples of the nucleotide may include ATP, UTP, GTP, and CTP, preferably an equimolar mixture of these four kinds. A preferred example of the derived product of pyruvic acid may be sodium pyruvate.

Specific examples of the keratinocyte basal medium may include a defined keratinocyte serum-free medium (DKSFM medium) (manufactured by Life Technologies) and EpiLife (registered trademark in Japan) medium. Of those, a preferred example may be a DKSFM medium. The DKSFM medium has a calcium concentration of 0.10 mM or less.

A particularly preferred example of the keratinocyte growth medium to be used in the production method of the present invention may be a medium obtained by supplementing the above-mentioned DKSFM medium with epidermal growth factor in the range of from 0.1 ng/mL to 1,000 ng/mL, preferably the range of from 1 ng/mL to 100 ng/mL, more preferably the range of from 5 ng/mL to 20 ng/mL, and cholera toxin in the range of from 1 μg/mL to 10 mg/mL, preferably the range of from 10 μg/mL to 1 mg/mL, more preferably the range of from 50 μg/mL to 200 μg/mL.

The timing at which the culture of the cell obtained in the step A in the medium (in particular, the keratinocyte growth medium) is initiated is not particularly limited as long as the lacrimal gland epithelial cell can be produced. The timing may fall within, for example, the range of from 0 hours to 36 hours after the completion of the transfection of the genes or proteins in the present invention in the step A, and from the viewpoint of obtaining better production efficiency of the lacrimal gland epithelial cell, may preferably fall within, for example, the range of from 12 hours to 24 hours after the completion of the transfection. In addition, as an example of the timing of the initiation of the culture given from another aspect, the timing may fall within, for example, the range of from 8 hours to 48 hours after the initiation of the first transfection of the genes or proteins in the present invention in the step A, and from the viewpoint of obtaining better production efficiency of the lacrimal gland epithelial cell, the timing may preferably fall within, for example, the range of from 12 hours to 36 hours after.

In the step B, the period of time for which the cell is cultured in the medium (in particular, the keratinocyte growth medium) is not particularly limited as long as the lacrimal gland epithelial cell can be produced. However, culture for too long a period of time reduces the production efficiency of the lacrimal gland epithelial cell, and hence the period of time may fall within, for example, the range of from 2 days to 6 days, preferably the range of from 2 days to 3 days.

The "lacrimal gland epithelial cell" to be produced in the present invention means a cell in which the expression of one kind or two or more kinds (preferably three or more kinds) of lacrimal gland epithelial cell marker genes is elevated and which is inducible into a lacrimal gland organ together with a lacrimal gland mesenchymal cell. Examples of the lacrimal gland epithelial cell marker genes may include fibroblast growth factor 5 (FGF5), left-right determination factor 2 (LEFTY2), fibroblast growth factor 10 (FGF10), Barx homeobox 2 (Barx2), cytokeratin 15 (Krt15), aquaporin 5 (AQP5), and lactoferrin (LTF). The cell in which "the expression of a lacrimal gland epithelial cell marker gene is elevated" means a cell in which the mRNA or protein expression level of the lacrimal gland epithelial cell marker gene is elevated as compared to the mRNA or protein expression level of the lacrimal gland epithelial cell marker gene in a cell before the expression of the genes in the present invention has been increased therein, or before the proteins in the present invention have been transfected thereinto.

In addition, whether or not a given cell is the above-mentioned "cell which is inducible into a lacrimal gland organ together with a lacrimal gland mesenchymal cell" may be confirmed by, for example, co-culturing the cell with a lacrimal gland germ. As a method for such co-culture, there may be preferably given a method described in Non Patent Literature 1.

<Lacrimal Gland Epithelial Cell of the Present Invention>

A lacrimal gland epithelial cell of the present invention is not particularly limited as long as the lacrimal gland epithelial cell is produced by the production method of the present invention. The description and suitable modes in the production method of the present invention apply also in the lacrimal gland epithelial cell of the present invention.

<Reagent Kit for Inducing Differentiation>

A reagent kit for inducing differentiation from a pluripotent stem cell into a lacrimal gland epithelial cell in the present invention (hereinafter sometimes referred to as "reagent kit for inducing differentiation of the present invention") is not particularly limited as long as the reagent kit for inducing differentiation of the present invention includes the following (a) and (b). The reagent kit for inducing differentiation of the present invention is an invention of use in which the following (a) and (b) are used in a specific use (reagent kit for inducing differentiation from a pluripotent stem cell into a lacrimal gland epithelial cell), and is not an invention of a mere combination of the following (a) and (b):

(a) a polynucleotide encoding PAX6 protein, or PAX6 protein; and (b) a polynucleotide encoding FOXC1 protein, or FOXC1 protein, or a polynucleotide encoding FOXP1 protein, or FOXP1 protein.

The reagent kit for inducing differentiation of the present invention preferably further includes (c) a polynucleotide encoding SIX1 protein, or SIX1 protein.

A preferred example of the polynucleotides in the reagent kit for inducing differentiation of the present invention may be mRNAs.

The weight ratio of the polynucleotides or the proteins to be included in the reagent kit for inducing differentiation of the present invention may be, for example, the weight ratio of the transfection amount of the polynucleotides or the proteins described above in the production method of the present invention.

The description and suitable modes in the production method of the present invention apply also in the reagent kit for inducing differentiation of the present invention.

The present invention is hereinafter described in detail by way of Examples, but the present invention is not limited to these Examples.

EXAMPLE 1

1. Analysis of Factors Specifically Expressed in Lacrimal Gland Epithelial Cells In order to identify factors associated with the induction of differentiation from stem cells into lacrimal gland epithelial cells, gene expression in lacrimal gland epithelial cells isolated from mouse lacrimal gland germs was comprehensively analyzed with a commercially available DNA microarray. The expression pattern obtained by the analysis was compared to expression patterns in lacrimal gland epithelium and lacrimal gland mesenchyme derived from the lacrimal gland germs, Harderian gland epithelium and Harderian gland mesenchyme derived from Harderian gland germs, embryonic palpebral conjunctival epithelium and mesenchyme, and an adult lacrimal gland and an adult Harderian gland, and genes considered to be specific to lacrimal gland epithelial cells were searched for. The inventors of the present invention found, out of those genes, the Six2 gene and the Foxc1 gene as transcription factor genes particularly highly expressed in lacrimal gland epithelial cells.

In order to seek transcription factors potentially associated with the induction of differentiation into lacrimal gland epithelial cells other than the foregoing, transcription factors exhibiting behavior similar to that of the Six2 gene were searched for on the basis of the above-mentioned expression patterns. As a result, the inventors of the present invention found Six1 gene, Six4 gene, and Foxc2 gene. In addition, the inventors of the present invention focused also on Pax6 gene. Further, the inventors of the present invention focused also on Foxp1 gene, Runx1 gene, and ILF2 gene as transcription factor genes exhibiting expression tendencies similar to that of the Foxc1 gene.

Thus, the inventors of the present invention found nine kinds of genes, i.e., the Six2 gene, the Foxc1 gene, the Six1 gene, the Six4 gene, the Foxc2 gene, the Pax6 gene, the Foxp1 gene, the Runx1 gene, and the ILF2 gene as candidates for transcription factors capable of inducing the differentiation of pluripotent stem cells into lacrimal gland epithelial cells.

In addition, in order to investigate a cell surface protein characteristic of lacrimal gland epithelial cells, gene expression of various cytokeratins in lacrimal gland epithelial cells isolated from mouse lacrimal gland germs was analyzed with a commercially available DNA microarray. The expression pattern obtained by the analysis was compared to expression patterns in cells of surrounding related tissues, and a cytokeratin considered to be characteristic of lacrimal gland epithelial cells was searched for. As a result, the inventors of the present invention found the gene of cytokeratin 15 (Krt15 gene). It has heretofore not been known that Krt15 is characteristically expressed in lacrimal gland epithelial cells, and it has been revealed that Krt15 gene is one novel lacrimal gland epithelial cell marker gene.

Lacrimal gland epithelial cells were stained with anti-Krt15 polyclonal antibodies, and as a result, it was confirmed that cytokeratin 15 was actually expressed on the surfaces of the lacrimal gland epithelial cells.

EXAMPLE 2

2. Search for Transcription Factors Capable of Inducing Differentiation of Pluripotent Stem Cells into Lacrimal Gland Epithelial Cells In order to search for transcription factors capable of inducing differentiation of pluripotent stem cells into lacrimal gland epithelial cells, the mRNAs of the nine kinds of candidate genes found in Example 1 (Six2 gene, Foxc1 gene, Six1 gene, Six4 gene, Foxc2 gene, Pax6 gene, Foxp1 gene, Runx1 gene, and ILF2 gene) were produced. The mRNAs were transfected into pluripotent stem cells, and it was confirmed whether or not differentiation into lacrimal gland epithelial cells was able to be induced.

[Production of mRNAs of Candidate Genes]

Sequence information on the above-mentioned nine kinds of candidate genes in a human was obtained from the website of NCBI, and a primer set capable of amplifying each gene was produced on the basis of its respective sequence information. Of the candidate genes, sequence information on human Pax6 has an accession number of NM_000280.4, sequence information on human Foxc1 has an accession number of NM_001453.2, sequence information on human Foxp1 has an accession number of NM_032682.5, and sequence information on human Six1 has an accession number of NM_005982.3. In addition, the SEQ ID NOS of the nucleotide sequences of the primer sets capable of amplifying those four kinds of candidate genes out of the nine kinds of candidate genes are shown in Table 1 below.

TABLE 1

| Gene name | Forward primer | Reverse primer |
|---|---|---|
| Pax6 | SEQ ID NO: 9 | SEQ ID NO: 10 |
| Foxc1 | SEQ ID NO: 11 | SEQ ID NO: 12 |
| Foxp1 | SEQ ID NO: 13 | SEQ ID NO: 14 |
| Six1 | SEQ ID NO: 15 | SEQ ID NO: 16 |

With use of a human genome sequence as a template, PCR was performed using each of the above-mentioned primer sets to amplify DNA fragments of each of the genes of interest. The amplified DNA fragments were each incorporated into a pCR2-UTR-R1R2 plasmid vector, and then it was confirmed that the DNA fragments were fragments of the genes of interest. The genes of interest were purified from the respective plasmid vectors containing the genes, and used as templates for in vitro transcription. To the templates, GTP, ATP, Me-CTP, Pseudo UTP, and a tail sequence were added to perform an in vitro transcription reaction (AMBION IVT KIT, manufactured by Life Technologies). Each synthetic mRNA generated by the in vitro transcription reaction was purified, and then its sequence was confirmed with a sequencer. Thus, the mRNAs of the above-mentioned nine kinds of candidate genes were obtained.

[Transfection of Synthetic mRNAs into Pluripotent Stem Cells]

Human ES cells were prepared as pluripotent stem cells. A medium was added to a laminin-coated culture dish (manufactured by Corning), the ES cells were seeded at $1\times10^4$ cells/cm$^2$, and culture was initiated. As the medium, a medium obtained by supplementing a culture medium for pluripotent stem cells, STEM FIT (registered trademark in Japan) (manufactured by Ajinomoto Co., Inc.), with 10 μM Y27632 (manufactured by Wako Pure Chemical Industries, Ltd.) was used. On the day after the initiation of the culture (1st day after the initiation of the culture), the medium was exchanged to STEM FIT (registered trademark in Japan) containing 0.25 μg/mL B18R protein (manufactured by Affymetrix Japan K.K.). After that, the mRNA of a candidate gene, Lipofectamin (registered trademark in Japan) 2000 (manufactured by Life Technologies), and Opti-MEM (registered trademark in Japan) (manufactured by Life Technologies) were added to and mixed with the medium at 1 μg/3 cm$^2$, 2 μL/3 cm$^2$, and 200 μL/3 cm$^2$, respectively, and culture was continued for 2 hours. Thus, the mRNA of the candidate gene was transfected into the ES cells (i.e., first transfection). The number of cells per 1 cm$^2$ of the culture dish was about 10,000, and hence the addition amount of the mRNA of the above-mentioned candidate gene to the medium is 33.33 pg/l cell.

When the mRNA of one kind of candidate gene was used as the mRNA of the candidate gene, 3 hours after the completion of its first transfection, the mRNA of the same kind of candidate gene (1 μg/3 cm$^2$) was added to and mixed with the medium, and culture was continued for 2 hours, to thereby perform the second transfection of the mRNA into the ES cells.

Meanwhile, when the mRNAs of two kinds or three kinds of candidate genes were used as the mRNA of the candidate gene, 3 hours after the completion of the transfection (first transfection) of the mRNA of the first kind of candidate gene, "the mRNA of the second kind of candidate gene (1 μg/3 $cm^2$)" or "the mRNAs of the second kind and third kind of candidate genes (1 μg/3 $cm^2$ per one kind of candidate gene mRNA)" were added to and mixed with the medium, and culture was continued for 2 hours, to thereby transfect "the mRNA of the second kind of candidate gene" or "the mRNAs of the second kind and third kind of candidate genes" into the ES cells.

In all the cases where one to three kinds of mRNAs of candidate genes were transfected, the same operation as the mRNA-transfecting operation performed on the first day of the transfection (2 times in total of transfection) was repeated on the day after that (1st day after the initiation of the transfection, i.e., 2nd day after the initiation of the culture).

When mRNA is transfected into the ES cells by the above-mentioned method, the mRNA is actually translated in the cells to generate a protein. This has already been confirmed by fluorescence staining of the protein. In addition, it has also been confirmed that most of the protein generated by transfecting the mRNA disappears in about 24 hours from the transfection.

[Culture of Cells after Synthetic mRNA Transfection in Keratinocyte Growth Medium]

On the 2nd day after the initiation of the transfection of the mRNA (3rd day after the initiation of the culture), the medium was exchanged to a medium obtained by supplementing a DKSFM medium (manufactured by Life Technologies) with 10 ng/mL epidermal growth factor (EGF) (manufactured by PeproTech) and 100 μg/mL cholera toxin (manufactured by List Biological Laboratories), and culture was continued.

[Confirmation of Presence or Absence of Increases in Expression of Lacrimal Gland Epithelial Cell Marker Genes]

After the transfection of the mRNAs of the candidate genes, culture was performed in a keratinocyte growth medium in accordance with the method described above in [Culture of Cells after Synthetic mRNA Transfection in Keratinocyte Growth Medium]. On the 2nd day after the initiation of the transfection of the mRNAs (day 2) (3rd day after the initiation of the culture) or 5th day thereafter (day 5) (6th day after the initiation of the culture), the cells were isolated, and whether the expression of lacrimal gland epithelial cell marker genes was increased in such cells was confirmed at mRNA level (transcription level). In addition, as negative controls, the expression levels ("hES day0") of the marker genes in cells on the day of the transfection of the mRNAs (1st day after the initiation of the culture) before the transfection of the mRNAs, and the expression levels ("hES DKSFM day6") of the marker genes in cells on day 6, the cells having been treated and cultured in the same manner except that the mRNAs were not transfected, were also measured. As the above-mentioned lacrimal gland epithelial cell marker genes, Pax6, Six1, Foxc1, Foxp1, FGF5, LEFTY2, FGF10, Barx2, Krt15, and AQP5 were used.

The expression levels of the mRNAs of the lacrimal gland epithelial cell marker genes were measured by extracting total RNA from the cells, and performing a real-time PCR method with Takara SYBR (registered trademark in Japan) Premix Ex Taq™ II (Takara Bio) and Thermal Cycler Dice (registered trademark in Japan) Real Time System (Takara Bio).

The mRNAs of the above-mentioned nine kinds of candidate genes were each transfected, one kind at a time, into pluripotent stem cells in accordance with the method described above in [Transfection of Synthetic mRNAs into Pluripotent Stem Cells], followed by culture in a keratinocyte growth medium in accordance with the method described above in [Culture of Cells after Synthetic mRNA Transfection in Keratinocyte Growth Medium]. However, even when the mRNA of any of the candidate genes was transfected, increases in expression of the lacrimal gland epithelial cell marker genes were not observed. Thus, it was revealed that differentiation into lacrimal gland epithelial cells was not able to be induced by increasing the expression of only one kind of those candidate genes.

Figure 1:
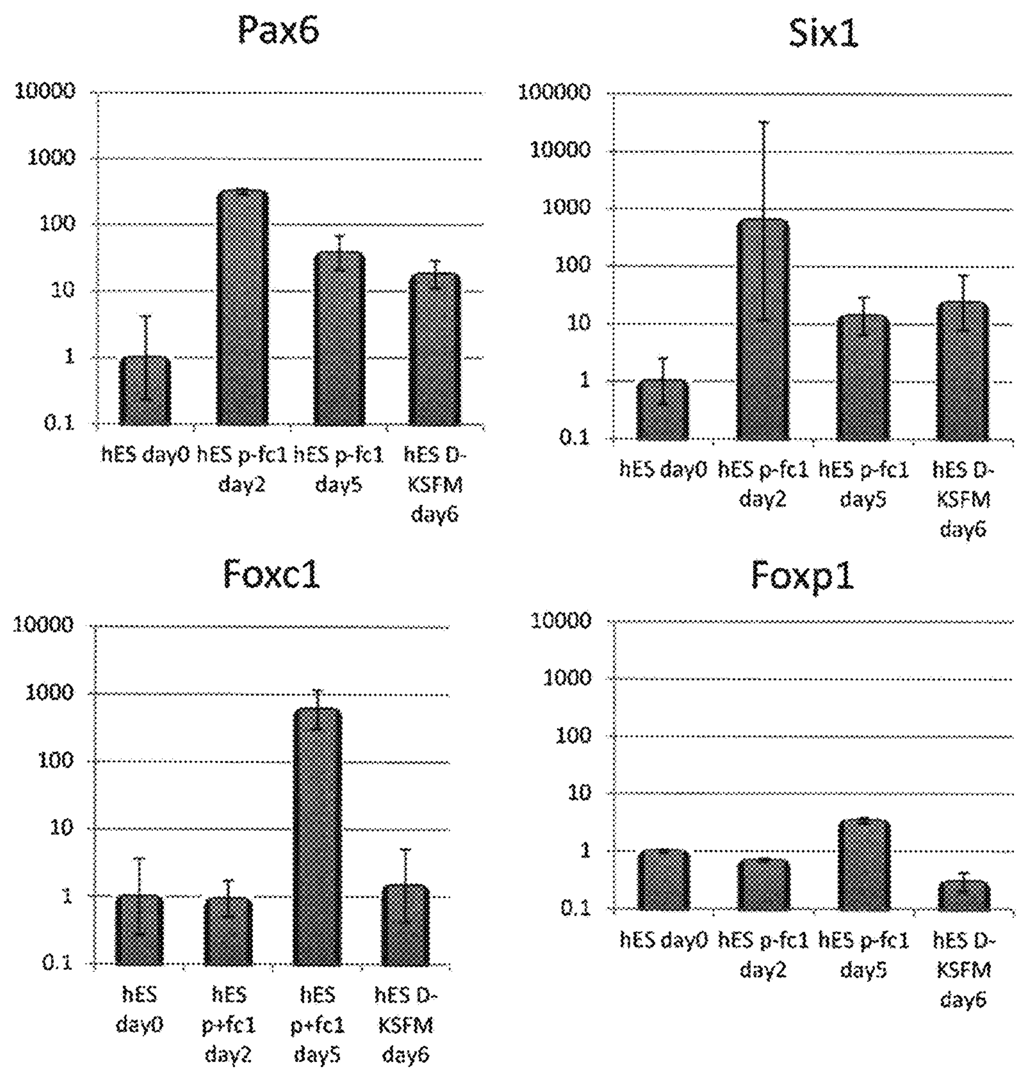
FIG. 1 are graphs for showing the results of measurement of the expression levels of lacrimal gland epithelial cell marker genes in cells in the case of transfecting the mRNAs of "Pax6 and Foxc1" into human ES cells, followed by culture in a keratinocyte growth medium. "hES p-fc1 day2" represents the results of cells on the 2nd day after the initiation of the transfection of the mRNAs, and "hES p-fc1 day5" represents the results of cells on the 5th day after the initiation of the transfection of the mRNAs. In addition, "hES day0" represents the results of cells on the day of the transfection of the mRNAs (1st day after the initiation of the culture) before the transfection of the mRNAs, and "hES DKSFM day6" represents the results of cells on day 6, the cells having been treated and cultured in the same manner except that the mRNAs were not transfected.
Figure 2:
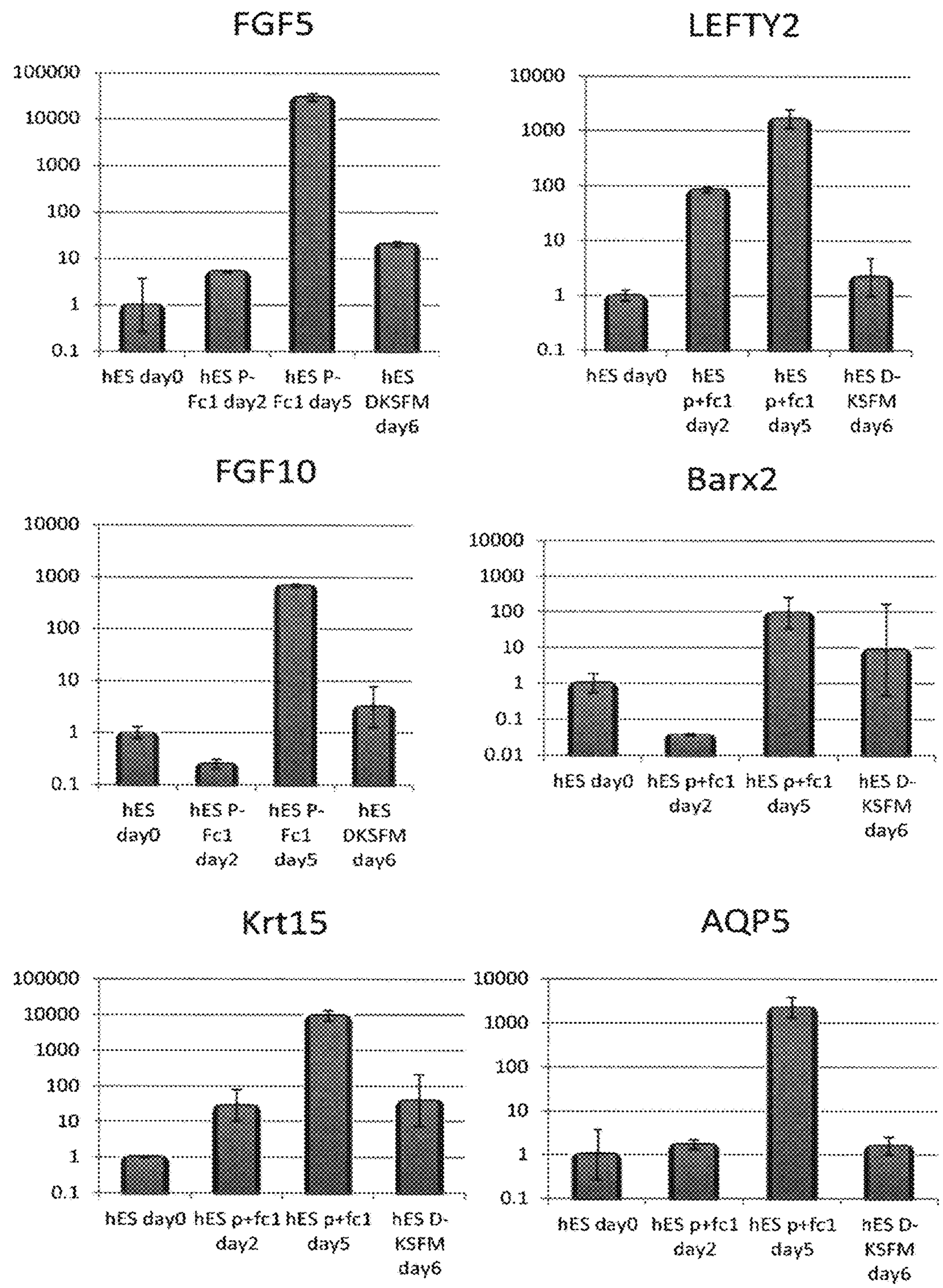
FIG. 2 are graphs for showing the results of measurement of the expression levels of lacrimal gland epithelial cell marker genes different from those shown in FIG. 1 in cells similar to those of FIG. 1.
Figure 4:
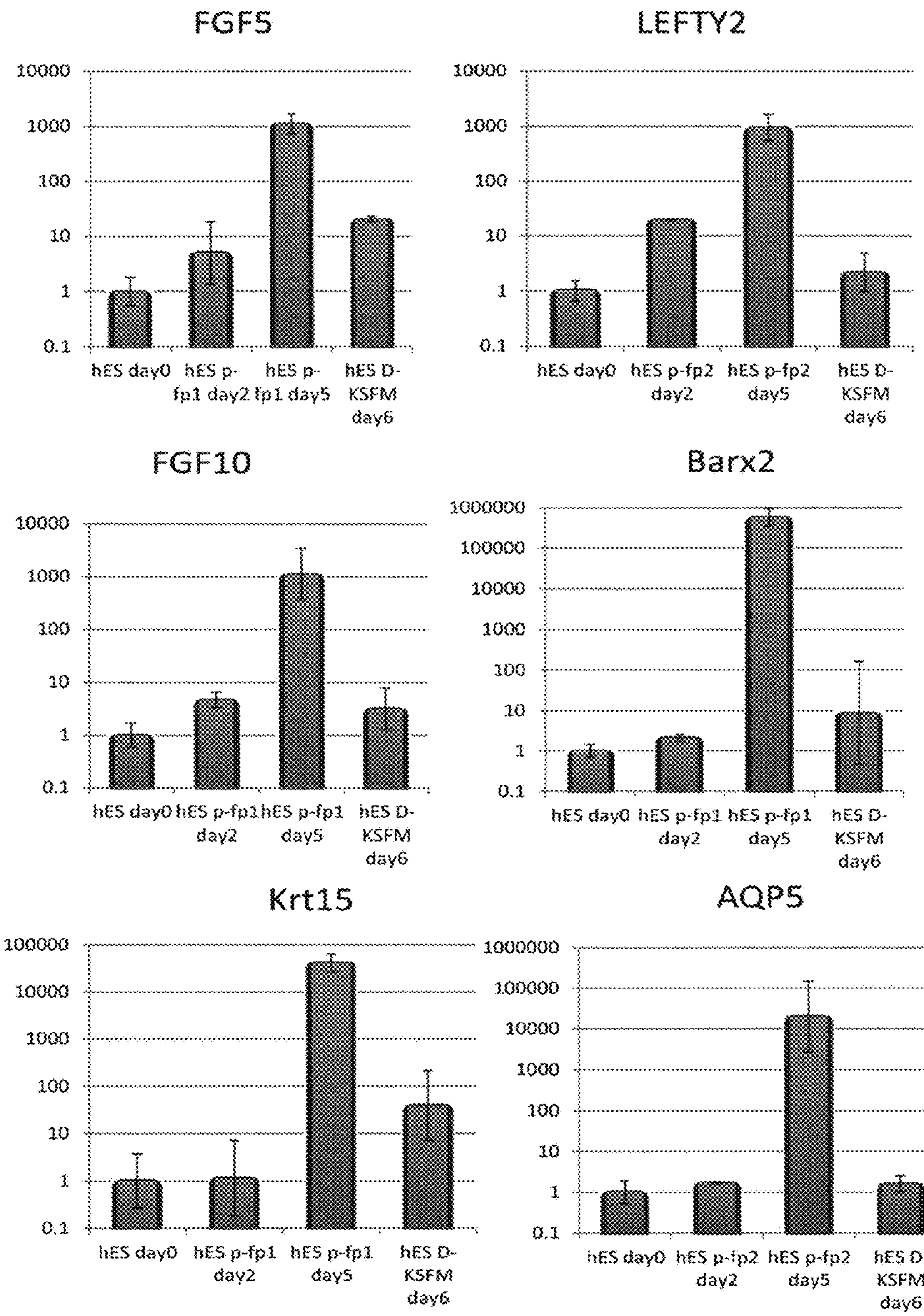
FIG. 4 are graphs for showing the results of measurement of the expression levels of lacrimal gland epithelial cell marker genes different from those shown in FIG. 3 in cells similar to those of FIG. 3.

Next, the transfection of the mRNAs of two kinds of candidate genes at a time out of the nine kinds of candidate genes was tested. Some combinations out of the tested combinations, and the presence or absence of increases in expression of the lacrimal gland epithelial cell marker genes in those cases are shown in Table 2 below. Further, the expression levels of the lacrimal gland epithelial cell marker genes in the case where the mRNAs of the candidate genes transfected were "Pax6/Foxc1" are shown in FIG. 1 and FIG. 2, and the expression levels of the lacrimal gland epithelial cell marker genes in the case of "Pax6/Foxp1" are shown in FIG. 3 and FIG. 4. In each combination of the candidate genes, the gene name written on the left is the candidate gene whose mRNA was transfected in the first transfection on the first day of the transfection, and the gene name written on the right is the candidate gene whose mRNA was transfected in the second transfection on the first day of the transfection. A similar operation to the transfection operation of the first day of the transfection was repeated on the day after the transfection (1st day after the initiation of the transfection).

TABLE 2

| | Combination of candidate genes transfected | Presence or absence of increase in expression of lacrimal gland epithelial cell marker gene |
|---|---|---|
| 1 | Pax6/Pax6 | x |
| 2 | Foxc1/Foxc1 | x |
| 3 | Pax6/Foxc1 | ○ |
| 4 | Pax6/Six1 | x |
| 5 | Pax6/Runx1 | x |
| 6 | Pax6/ILF2 | x |
| 7 | Pax6/Foxp1 | ○ |
| 8 | Foxp1/Foxp1 | x |
| 9 | None (negative control) | x |

As apparent from the results shown in Table 2 and FIG. 1 to FIG. 4, and the like, increases in expression of the lacrimal gland epithelial cell marker genes were able to be confirmed when the mRNAs of the candidate genes transfected were in specific combinations, i.e., only in the case of "Pax6/Foxc1" and the case of "Pax6/Foxp1". Further, when the expression levels of the lacrimal gland epithelial cell marker genes in the case of "Pax6/Foxp1" are confirmed, it is found that the expression of Foxc1 is increased. Thus, it was revealed that the FOXP1 protein was a transcription factor functioning upstream of the FOXC1 protein in a signaling pathway. Those results revealed that transcription factors essential for inducing differentiation into lacrimal gland epithelial cells by being transfected into pluripotent stem cells were PAX6 and FOXC1.

After the transfection of Pax6 mRNA and Foxc1 mRNA into the ES cells, the cells were cultured in a keratinocyte growth medium in accordance with the method described above in [Culture of Cells after Synthetic mRNA Transfection in Keratinocyte Growth Medium]. On the 5th day after the initiation of the transfection of the mRNAs, the cells were isolated, and the expression of lacrimal gland epithelial cell marker proteins was confirmed by an immunohistological staining method. As a result, the expression of the respective proteins corresponding to the expression of the mRNAs of the lacrimal gland epithelial cell marker genes was able to be confirmed.

[Transfection of mRNAs of Three Kinds of Transcription Factors]

While the above-mentioned experiment revealed that transcription factors essential for inducing differentiation into lacrimal gland epithelial cells by being transfected into pluripotent stem cells were PAX6 and FOXC1, an investigation was made as to whether or not there was a transcription factor providing better results in the case of transfecting the mRNA of another kind (third kind) of transcription factor in addition to the mRNAs of the two kinds of transcription factors.

Figure 5:
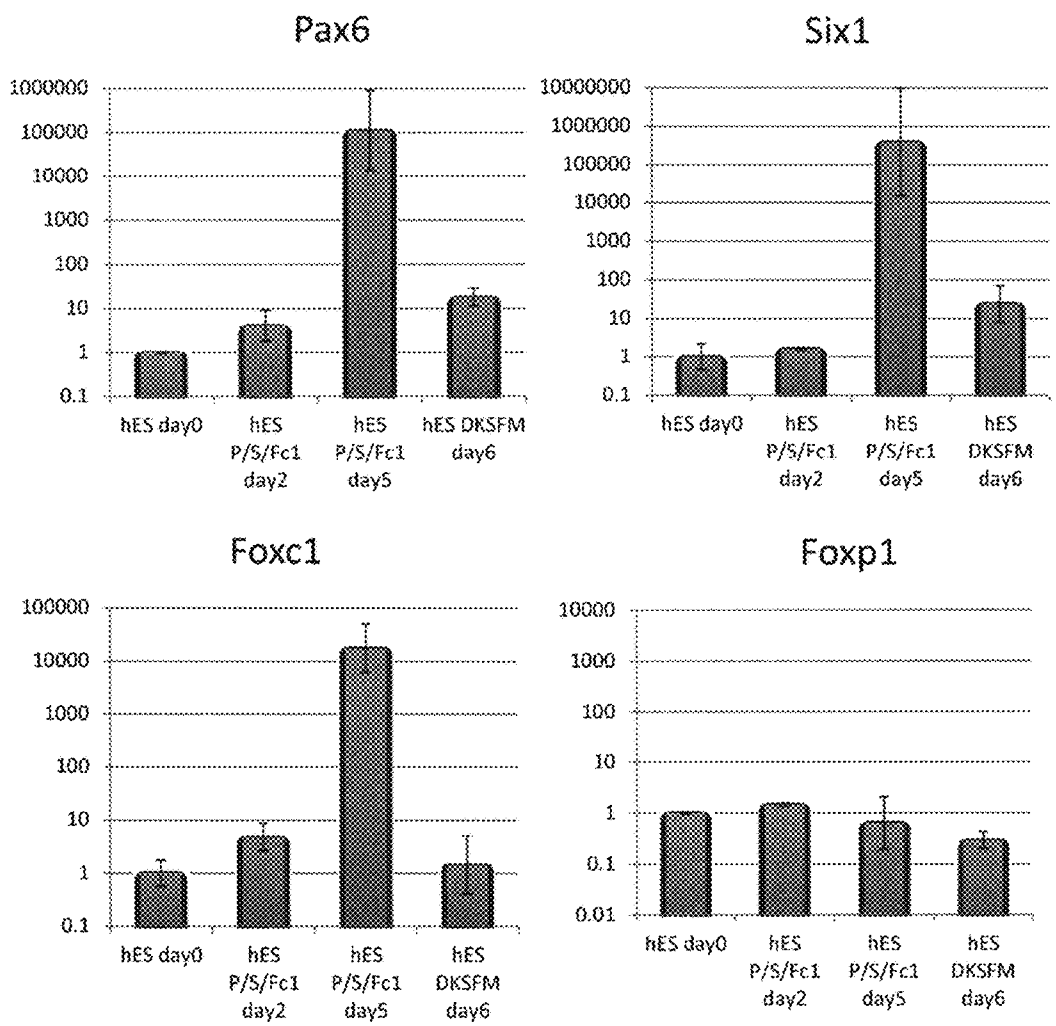
FIG. 5 are graphs for showing the results of measurement of the expression levels of lacrimal gland epithelial cell marker genes in cells in the case of transfecting the mRNAs of "Pax6, Foxc1, and Six1" into human ES cells, followed by culture in a keratinocyte growth medium. "hES P/S/Fc1 day2" represents the results of cells on the 2nd day after the initiation of the transfection of the mRNAs, and "hES P/S/Fc1 day5" represents the results of cells on the 5th day after the initiation of the transfection of the mRNAs. In addition, "hES day0" represents the results of cells on the day of the transfection of the mRNAs (1st day after the initiation of the culture) before the transfection of the mRNAs, and "hES DKSFM day6" represents the results of cells on day 6, the cells having been treated and cultured in the same manner except that the mRNAs were not transfected.
Figure 6:
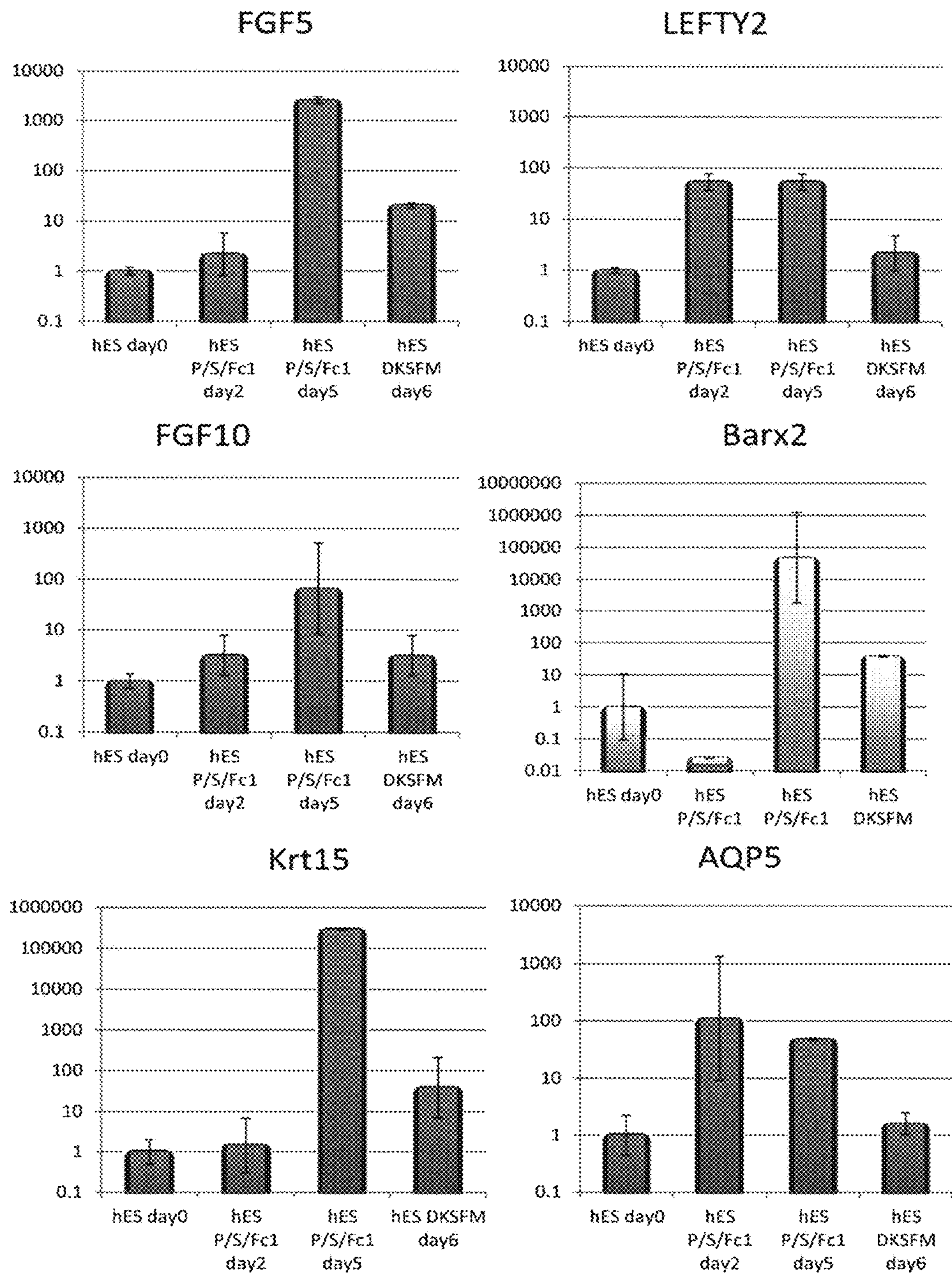
FIG. 6 are graphs for showing the results of measurement of the expression levels of lacrimal gland epithelial cell marker genes different from those shown in FIG. 5 in cells similar to those of FIG. 5.
Figure 7:
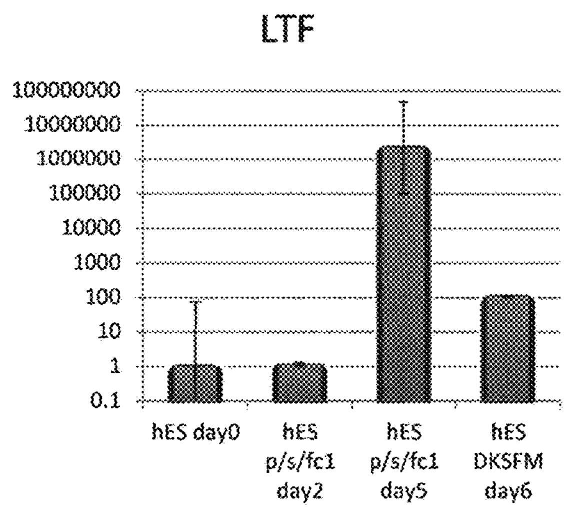
FIG. 7 is a graph for showing the results of measurement of the expression levels of lacrimal gland epithelial cell marker genes different from those shown in FIG. 5 and FIG. 6 in cells similar to those of FIG. 5.

As the mRNA of the third kind of transcription factor, the mRNA of Six1, Runx1, ILF2, or the like was used. The mRNAs of three kinds of transcription factors were transfected into ES cells in accordance with the method described above in [Transfection of Synthetic mRNAs into Pluripotent Stem Cells], followed by culture in a keratinocyte growth medium in accordance with the method described above in [Culture of Cells after Synthetic mRNA Transfection in Keratinocyte Growth Medium]. On the 5th day after the initiation of the transfection of the mRNAs, the cells were isolated, and the expression levels of the lacrimal gland epithelial cell marker genes were measured in accordance with the method described above in [Confirmation of Presence or Absence of Increases in Expression of Lacrimal Gland Epithelial Cell Marker Genes]. As a result, it was revealed that the case of using Six mRNA as the mRNA of the third kind of transcription factor was preferred. The expression levels of the lacrimal gland epithelial cell marker genes in the case of transfecting three kinds of mRNAs, i.e., Pax6 mRNA, Foxc1 mRNA, and Six1mRNA into ES cells are shown in FIG. 5 to FIG. 7. In the case of transfecting three kinds of mRNAs, i.e., Pax6 mRNA, Foxc1 mRNA, and Six1 mRNA into ES cells, as compared to the case of transfecting two kinds of mRNAs, i.e., Pax6 mRNA and Foxc1 mRNA, the expression of Pax6 on day 5, Six1 on day 5, Foxc1 on day 2 and day 5, Barx2 on day 5, Krt15 on day 5, and AQP5 on day 2 was increased (see FIG. 1 and FIG. 2, and FIG. 5 and FIG. 6).

[Confirmation of Expression of Lacrimal Gland Epithelial Cell Marker Proteins in the Case of transfecting mRNAs of Specific Three Kinds of Transcription Factors]

As described above, the expression of the lacrimal gland epithelial cell markers is increased in cells obtained by transfecting the mRNAs of the specific three kinds of transcription factors (PAX6, FOXC1, and SIX1) into ES cells, followed by culture in a keratinocyte growth medium. Whether lacrimal gland epithelial cell marker proteins were actually expressed in cells on the 5th day after the initiation of the transfection of the mRNAs was confirmed by an immunohistological staining method. As the lacrimal gland epithelial cell marker proteins to be confirmed, lactoferrin (LTF), cytokeratin 15 (KRT15), aquaporin 5 (AQP5), fibroblast growth factor 10 (FGF10), and BARX2 were targeted. The results of such immunohistological staining are shown in FIG. 8.

Figure 8:
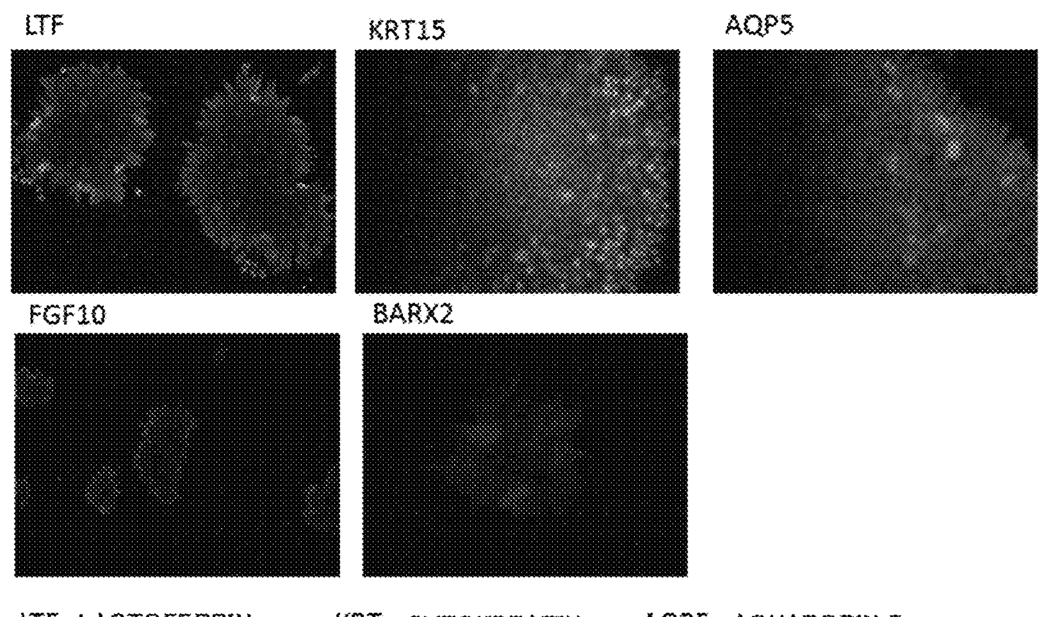
FIG. 8 are photographs for showing the results of immunohistological staining of cells in the case of transfecting the mRNAs of specific three kinds of transcription factors (PAX6, FOXC1, and SIX1) into human ES cells, followed by culture in a keratinocyte growth medium. In the upper left of each panel, the name of a protein serving as a staining target is shown.

As apparent from the results shown in FIG. 8, it was shown that each of the lacrimal gland epithelial cell marker proteins was actually expressed in the cells.

EXAMPLE 3

Figure 9:
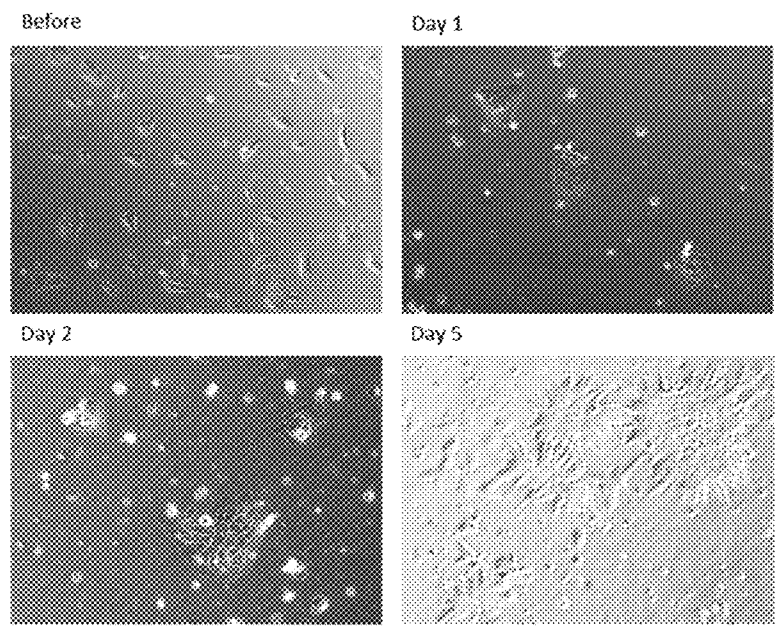
FIG. 9 are photographs for showing the results of observation with a phase-contrast microscope of the morphology of cells in the case of transfecting the mRNAs of the specific three kinds of transcription factors (PAX6, FOXC1, and SIX1) into human ES cells, followed by culture. In the upper left panel, the morphology of cells immediately before the transfection of the mRNAs is shown. In the upper right panel, the morphology of cells on Day 1 (1st day after the initiation of the transfection of the mRNAs) is shown. In the lower left panel, the morphology of cells on Day 2 (2nd day after the initiation of the transfection of the mRNAs) is shown. In the lower right panel, the morphology of cells on Day5 (5th day after the initiation of the transfection of the mRNAs) is shown.

3. Confirmation of Morphological Change of Human ES Cells etc. by transfection of mRNAs of Specific Transcription Factors In Example 2, it has been described that, when the mRNAs of specific two kinds or three kinds of transcription factors are transfected into pluripotent stem cells, followed by culture in a keratinocyte growth medium, the expression of the lacrimal gland epithelial cell marker genes increases. The results of observation with a phase-contrast microscope of a morphological change of cells in the case of transfecting the mRNAs of the specific three kinds of transcription factors (Pax6, Foxc1, and Six1) into pluripotent stem cells, followed by culture in a keratinocyte growth medium are shown in FIG. 9. As apparent from FIG. 9, on the 5th day after the initiation of the transfection of the mRNAs (Day 5) (6th day after the initiation of the culture), the ES cells changed into cells of a morphology characteristic of lacrimal gland epithelial cells, i.e., a rectangular morphology extending outward in an elongate manner.

A similar morphological change was observed also in the case of transfecting, instead of the specific three kinds, the mRNAs of the specific two kinds ("Pax6 and Foxc1") of transcription factors into pluripotent stem cells, followed by culture in a keratinocyte growth medium. However, in the case of transfecting the mRNAs of the specific three kinds of transcription factors (Pax6, Foxc1, and Six1), the degree of the morphological change was amplified, and the morphological change was more distinct. Thus, it has been found that, when the differentiation of pluripotent stem cells into lacrimal gland epithelial cells is induced, the transfection of the mRNAs of the specific three kinds (Pax6, Foxc1, and Six1) is preferred because the direction of the differentiation into a lacrimal gland epithelial cell line can be made more distinct than in the transfection of the mRNAs of the specific two kinds ("Pax6 and Foxc1" or "Pax6 and Foxp1").

EXAMPLE 4

4. Confirmation of whether Obtained Lacrimal Gland Epithelial Cells have Ability to Regenerate Three-dimensional Structure of Lacrimal Gland An attempt was made to confirm whether or not the lacrimal gland epithelial cells derived by transfecting the mRNAs of transcription factors actually had an ability to regenerate the three-dimensional structure of a lacrimal gland organ.

The mRNAs of the specific three kinds of transcription factors (Pax6, Foxc1, and Six1) were transfected into ES cells in accordance with the method described above in [Transfection of Synthetic mRNAs into Pluripotent Stem Cells] of Example 2, followed by culture in a keratinocyte growth medium in accordance with the method described above in [Culture of Cells after Synthetic mRNA Transfection in Keratinocyte Growth Medium] of Example 2. Cells on the 5th day after the initiation of the transfection of the mRNAs were isolated as lacrimal gland epithelial cells.

Figure 10:
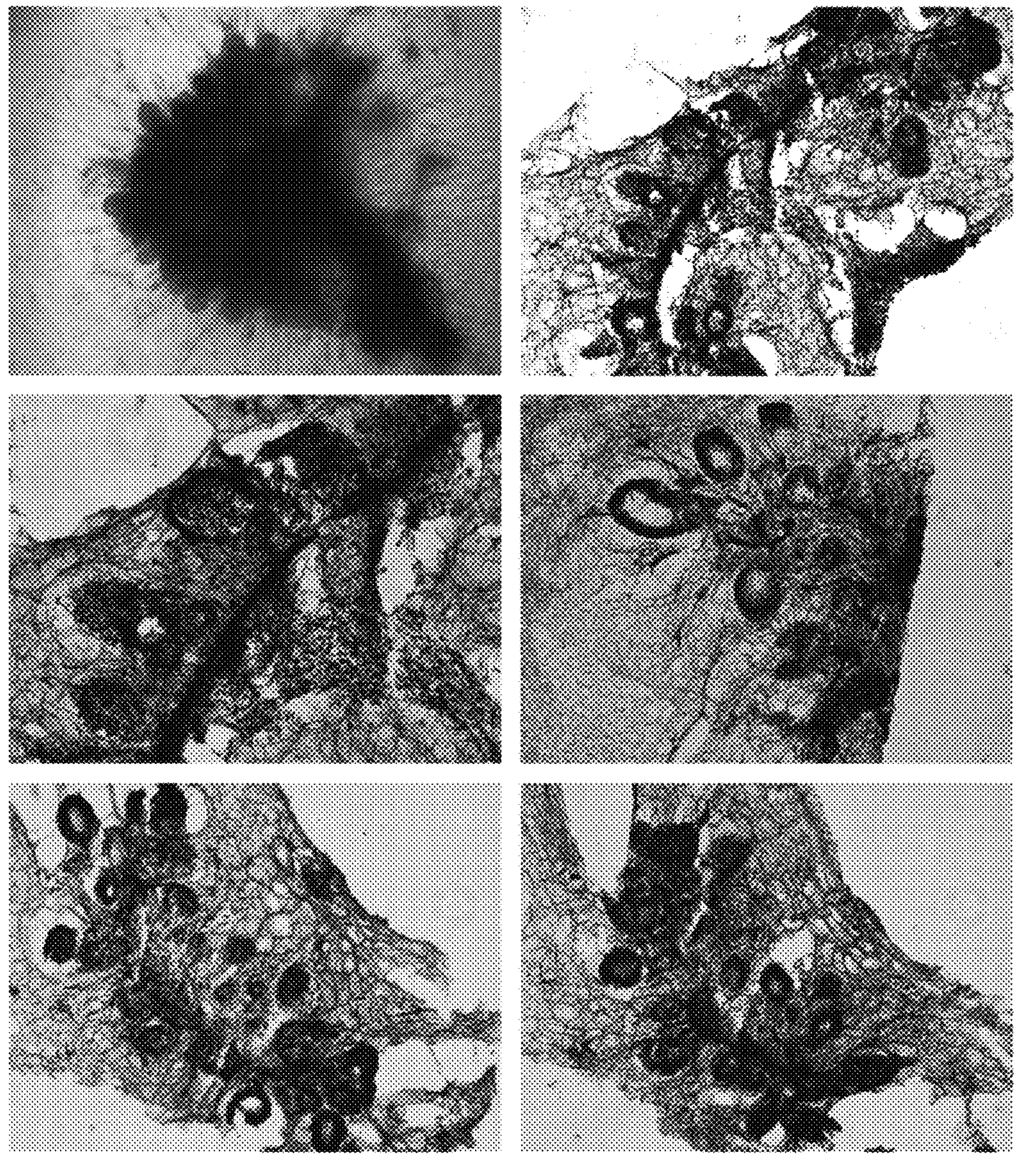
FIG. 10 are photographs for showing the results of observation of a cell mass obtained by three-dimensionally co-culturing lacrimal gland epithelial cells in the present invention and cells derived from a lacrimal gland germ. In the upper left panel, the result of observation with an optical microscope of the cell mass without any treatment is shown, and in the other panels, the results of observation with an optical microscope after hematoxylin and eosin staining of frozen sections of the cell mass are shown.

As described in Background Art, the formation of a lacrimal gland organ requires both lacrimal gland epithelial cells and lacrimal gland mesenchymal cells. In accordance with the method described in Non Patent Literature 1, lacrimal gland germs of embryonic day-16.5 mouse embryos were harvested, and cells of the lacrimal gland germs were isolated into individual cells. These cells and the above-mentioned lacrimal gland epithelial cells were three-dimensionally co-cultured, and as a result, a cell mass having a three-dimensional structure similar to a mature lacrimal gland (lacrimal gland organ) was formed. The result of observation of the cell mass with an optical microscope is shown in the upper left panel of FIG. 10, and the results of observation with an optical microscope after hematoxylin and eosin staining of frozen sections of the cell mass are shown in the other panels of FIG. 10. As apparent from FIG. 10, the cell mass produced by the above-mentioned method has been revealed to have three-dimensional structures similar to acini and ducts, which are structures characteristic of a mature lacrimal gland. Thus, it has been shown that the lacrimal gland epithelial cells produced by the method of the present invention actually have an ability to regenerate the three-dimensional structure of a lacrimal gland organ.

INDUSTRIAL APPLICABILITY

According to the present invention, lacrimal gland epithelial cells can be produced efficiently in a large amount within a short period of time from clinically applicable pluripotent stem cells (e.g., ES cells or iPS cells). In addition, the lacrimal gland epithelial cell produced by the present invention is a lacrimal gland epithelial cell having an ability to regenerate the three-dimensional structure of a lacrimal gland organ. When, in the future, not only the lacrimal gland epithelial cells, but also lacrimal glandmesenchymal cells can be produced efficiently in a large amount within a short period of time from pluripotent stem cells (e.g., ES cells or iPS cells), the possibility of the realization of regenerative medicine of a lacrimal gland organ will further increase. The method of producing a lacrimal gland epithelial cell in the present invention can be said to be a great step toward the possibility.

The invention claimed is:

1. A method of producing a human lacrimal gland epithelial cell expressing lactoferrin, cytokeratin 15, aquaporin 5, fibroblast growth factor 10 and Homeobox protein BarX-like 2 as cell markers in vitro, comprising the following step A:

Step A: a step including increasing expression of paired box 6 gene in a human embryonic stem cell or a human induced pluripotent stem cell, or transfecting paired box 6 protein thereinto, and increasing expression of forkhead box C1 gene or forkhead box P1 gene in the human embryonic stem cell or the human induced pluripotent stem cell, or transfecting forkhead box C1 protein or forkhead box P1 protein thereinto.

2. The method of producing a human lacrimal gland epithelial cell according to claim 1, wherein the step of increasing expression of paired box 6 gene comprises a step of transfecting a polynucleotide encoding paired box 6 protein into the human embryonic stem cell or the human induced pluripotent stem cell, wherein the step of increasing expression of forkhead box C1 gene comprises a step of transfecting a polynucleotide encoding forkhead box C1 protein into the human embryonic stem cell or the human induced pluripotent stem cell, and wherein the step of increasing expression of forkhead box P1 gene comprises a step of transfecting a polynucleotide encoding forkhead box P1 protein into the human embryonic stem cell or the human induced pluripotent stem cell.

3. The method of producing a human lacrimal gland epithelial cell according to claim 2, wherein the polynucleotide comprises mRNA.

4. The method of producing a human lacrimal gland epithelial cell according to claim 1, wherein the step A further includes increasing expression of SIX homeobox 1 gene in the human embryonic stem cell or the human induced pluripotent stem cell, or transfecting SIX homeobox 1 protein thereinto.

5. The method of producing a human lacrimal gland epithelial cell according to claim 4, wherein the increasing expression of SIX homeobox 1 gene comprises transfecting a polynucleotide encoding SIX homeobox 1 protein into the human embryonic stem cell or the human induced pluripotent stem cell.

6. The method of producing a human lacrimal gland epithelial cell according to claim 1, further comprising a step of culturing the cell obtained in the step A in a keratinocyte growth medium.

7. The method of producing a human lacrimal gland epithelial cell according to claim 6, wherein the keratinocyte growth medium contains epidermal growth factor and/or cholera toxin.

8. The method of producing a human lacrimal gland epithelial cell according to claim 6, wherein the keratinocyte growth medium has a calcium concentration of 0.15 mM or less.

9. A human lacrimal gland epithelial cell, which is produced by the method of claim 1.

10. The human lacrimal gland epithelial cell according to claim 9, which is further three-dimensionally co-cultured with a cell of a lacrimal gland germ, wherein the lacrimal gland epithelial cell has an ability to regenerate a three-dimensional structure of a lacrimal gland organ.

11. A reagent kit for inducing differentiation from a human pluripotent stem cell into a human lacrimal gland epithelial cell, comprising the following (a) and (b):

(a) a polynucleotide encoding paired box 6 protein, or paired box 6 protein; and (b) a polynucleotide encoding forkhead box C1 protein, or forkhead box C1 protein, or a polynucleotide encoding forkhead box P1 protein, or forkhead box P1 protein.

12. The reagent kit for inducing differentiation according to claim 11, further comprising (c) a polynucleotide encoding SIX homeobox 1 protein, or SIX homeobox 1 protein.

* * * * *